US009597465B2

(12) United States Patent
Striebig et al.

(10) Patent No.: US 9,597,465 B2
(45) Date of Patent: Mar. 21, 2017

(54) METHODS OF OPERATING AND FABRICATING INHALERS WITH AIRWAY DISKS HAVING DISCRETE AIRWAY CHANNELS

(71) Applicant: Oriel Therapeutics, Inc., Durham, NC (US)

(72) Inventors: Rachel Striebig, London (GB); Matthew Allen, London (GB); Thomas W. Ruckdeschel, Cary, NC (US); Charles A. Buckner, III, Chapel Hill, NC (US); Scott Alexander Lewis, Cambridge (GB); Andrew Murray Gow, Porirua (NZ); Jonathan David Tuckwell, Cambridge (GB)

(73) Assignee: Oriel Therapeutics, Inc., Durham, NC (US)

( * ) Notice: Subject to any disclaimer, the term of this patent is extended or adjusted under 35 U.S.C. 154(b) by 465 days.

(21) Appl. No.: 14/163,156

(22) Filed: Jan. 24, 2014

(65) Prior Publication Data
US 2014/0137864 A1 May 22, 2014

Related U.S. Application Data

(63) Continuation of application No. 13/735,532, filed on Jan. 7, 2013, now Pat. No. 8,671,938, which is a continuation of application No. 12/566,799, filed on Sep. 25, 2009, now Pat. No. 8,550,071.

(60) Provisional application No. 61/100,482, filed on Sep. 26, 2008, provisional application No. 61/148,520, filed on Jan. 30, 2009.

(51) Int. Cl.
*A61M 11/00* (2006.01)
*A61M 15/00* (2006.01)

(52) U.S. Cl.
CPC .... *A61M 15/0045* (2013.01); *A61M 15/0048* (2014.02); *A61M 15/0075* (2014.02); *Y10T 29/49826* (2015.01)

(58) Field of Classification Search
CPC .............. A61M 15/00; A61M 15/0045; A61M 15/0048; Y10T 29/49826
USPC ............ 128/203.12, 203.14, 200.14, 200.16, 128/200.23, 200.24, 203.15, 203.21, 128/203.19
See application file for complete search history.

(56) References Cited

U.S. PATENT DOCUMENTS 2,828,005 A 3/1958 Rinke et al.
4,307,734 A 12/1981 Blankenship
(Continued)

FOREIGN PATENT DOCUMENTS

CA 2506866 6/2004
DE 19500764 7/1996
(Continued)

OTHER PUBLICATIONS

Hickey et al., A new millennium for inhaler technology, 21 Pharm. Tech., n. 6, pp. 116-125 (1997).
(Continued)

*Primary Examiner* — Steven Douglas
(74) *Attorney, Agent, or Firm* — Myers Bigel, P.A.

(57) ABSTRACT

Methods of fabricating and operating dry powder inhalers that include dose disks and airway channel disks with sealant layers, the airway channel disks forming radially-extending discrete, typically dose-specific, airway channels serially forming a portion of the inhalation pathway to deliver dry powder to a user using the inhalers.

14 Claims, 35 Drawing Sheets

(56) References Cited

U.S. PATENT DOCUMENTS

| | | | |
|---|---|---|---|
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,138,138 A | 8/1992 | Theilacker et al. |
| 5,327,883 A | 7/1994 | Williams et al. |
| 5,337,740 A | 8/1994 | Armstrong et al. |
| 5,388,572 A | 2/1995 | Mulhauser et al. |
| 5,394,868 A | 3/1995 | Ambrosio et al. |
| 5,529,059 A | 6/1996 | Armstrong et al. |
| 5,533,502 A | 7/1996 | Piper |
| 5,590,645 A | 1/1997 | Davies et al. |
| 5,622,166 A | 4/1997 | Eisele et al. |
| 5,634,900 A | 6/1997 | Makino et al. |
| 5,715,810 A | 2/1998 | Armstrong et al. |
| 5,727,607 A | 3/1998 | Ichikawa et al. |
| 5,769,073 A | 6/1998 | Eason et al. |
| 5,860,419 A | 1/1999 | Davies et al. |
| 5,873,360 A | 2/1999 | Davies et al. |
| 5,909,829 A | 6/1999 | Wegman et al. |
| 5,921,237 A | 7/1999 | Eisele et al. |
| 5,947,169 A | 9/1999 | Wegman et al. |
| 6,029,663 A | 2/2000 | Eisele et al. |
| 6,032,666 A | 3/2000 | Davies et al. |
| 6,082,356 A | 7/2000 | Stradella |
| 6,116,237 A | 9/2000 | Schultz et al. |
| 6,116,238 A | 9/2000 | Jackson et al. |
| 6,245,339 B1 | 6/2001 | Van Oort et al. |
| 6,328,033 B1 | 12/2001 | Avrahami |
| 6,367,473 B1 | 4/2002 | Käfer |
| 6,378,519 B1 | 4/2002 | Davies et al. |
| 6,445,941 B1 | 9/2002 | Hampton et al. |
| 6,536,427 B2 | 3/2003 | Davies et al. |
| 6,543,448 B1 | 4/2003 | Smith et al. |
| 6,550,477 B1 | 4/2003 | Casper et al. |
| 6,591,832 B1 | 7/2003 | DeJonge |
| 6,655,381 B2 | 12/2003 | Keane et al. |
| 6,668,827 B2 | 12/2003 | Schuler et al. |
| 6,679,254 B1 | 1/2004 | Rand et al. |
| 6,792,945 B2 | 9/2004 | Davies et al. |
| 6,810,872 B1 | 11/2004 | Ohki et al. |
| 6,871,647 B2 | 3/2005 | Allan et al. |
| 6,880,555 B1 | 4/2005 | Brunnberg et al. |
| 6,889,690 B2 | 5/2005 | Crowder et al. |
| 6,915,802 B1 | 7/2005 | Anderson et al. |
| 6,923,178 B2 | 8/2005 | Snow |
| 6,948,494 B1 | 9/2005 | Snow |
| 7,089,935 B1 | 8/2006 | Rand |
| 7,219,665 B1 | 5/2007 | Braithwaite |
| 7,225,808 B2 | 6/2007 | Davies et al. |
| 7,275,538 B2 | 10/2007 | Nakamura |
| 7,318,436 B2 | 1/2008 | Snow |
| 7,389,775 B2 | 6/2008 | Davies et al. |
| 7,503,324 B2 | 3/2009 | Barney et al. |
| 7,571,723 B2 | 8/2009 | Braithwaite |
| 7,571,724 B2 | 8/2009 | Braithwaite |
| 7,669,597 B2 | 3/2010 | Sullivan et al. |
| 8,381,721 B2 | 2/2013 | Thoe et al. |
| 8,550,071 B2 | 10/2013 | Striebig et al. |
| 2001/0007853 A1 | 7/2001 | Dimarchi et al. |
| 2001/0053761 A1 | 12/2001 | Dimarchi et al. |
| 2002/0040713 A1 | 4/2002 | Eisele et al. |
| 2002/0170560 A1 | 11/2002 | Young et al. |
| 2003/0178024 A1 | 9/2003 | Allan et al. |
| 2004/0025877 A1 | 2/2004 | Crowder et al. |
| 2005/0056281 A1 | 3/2005 | Snow |
| 2005/0126568 A1 | 6/2005 | Davies et al. |
| 2005/0154491 A1 | 7/2005 | Andersan et al. |
| 2005/0161041 A1 | 7/2005 | Schuler et al. |
| 2005/0172963 A1 | 8/2005 | Allan et al. |
| 2006/0102511 A1 | 5/2006 | Pasbrig et al. |
| 2006/0157053 A1 | 7/2006 | Barney et al. |
| 2007/0062525 A1 | 3/2007 | Bonney et al. |
| 2007/0137643 A1 | 6/2007 | Bonney et al. |
| 2007/0137645 A1 | 6/2007 | Eason et al. |
| 2007/0181123 A1 | 8/2007 | Houzego |
| 2007/0181124 A1 | 8/2007 | Casper et al. |
| 2007/0215149 A1 | 9/2007 | King et al. |
| 2007/0221218 A1 | 9/2007 | Warden et al. |
| 2007/0235029 A1 | 10/2007 | Zhu et al. |
| 2008/0001008 A1 | 1/2008 | Thoemmes et al. |
| 2008/0127971 A1 | 6/2008 | King et al. |
| 2008/0223366 A1 | 9/2008 | Davies et al. |
| 2009/0114220 A1 | 5/2009 | Wachtel et al. |
| 2009/0139516 A1 | 6/2009 | Augustyn et al. |
| 2009/0194105 A1 | 8/2009 | Besseler et al. |
| 2010/0163042 A1 | 7/2010 | Bhowmick et al. |
| 2011/0162648 A1 | 7/2011 | Ruckdeschel |

FOREIGN PATENT DOCUMENTS

| | | |
|---|---|---|
| EP | 1106196 | 3/2001 |
| EP | 1779884 | 5/2007 |
| EP | 1844805 | 10/2007 |
| GB | 873410 | 7/1961 |
| GB | 2246299 | 1/1992 |
| GB | 2340758 | 3/2000 |
| WO | WO 94/14490 | 7/1994 |
| WO | WO 94/20164 | 9/1994 |
| WO | WO 98/41265 | 9/1998 |
| WO | WO 99/36116 | 7/1999 |
| WO | WO 00/45879 | 8/2000 |
| WO | WO 01/17595 | 3/2001 |
| WO | WO 01/28616 | 4/2001 |
| WO | WO 01/34234 | 5/2001 |
| WO | WO 02/053215 | 7/2002 |
| WO | WO 02/053216 | 7/2002 |
| WO | WO 03/011708 | 2/2003 |
| WO | WO 2004/045487 | 6/2004 |
| WO | WO 2005/002654 | 1/2005 |
| WO | WO 2005/037353 | 4/2005 |
| WO | WO 2005/044173 | 5/2005 |
| WO | WO 2005/110519 | 11/2005 |
| WO | WO 2006/031775 | 3/2006 |
| WO | WO 2006/108877 | 10/2006 |
| WO | WO 2007/007110 | 1/2007 |
| WO | WO 2007/012871 | 2/2007 |
| WO | WO 2008/039182 | 4/2008 |

OTHER PUBLICATIONS

Prime et al., Review of Dry Powder Inhalers, 26 Adv. Drug Delivery Rev., pp. 51-58 (1997).

Wolff et al., Generation of Aerosolized Drugs, J. Aerosol. Med., pp. 88-106 (1994).

European Search Report for European Application No. 09 816 585.5, Dated Feb. 1, 2012, 8 pages.

PCT Invitation to Pay Additional Fees and Partial Search for corresponding PCT Application No. PCT/US2009/058285, Date of Mailing Dec. 30, 2009.

PCT International Search Report and Written Opinion for PCT Application No. PCT/US2009/005321, Date of Mailing Mar. 29, 2010.

PCT International Search Report and Written Opinion for PCT Application No. PCT/US2009/005336, Date of Mailing May 4, 2010.

PCT International Search Report and Written Opinion for PCT Application No. PCT/US2009/005338, Date of Mailing May 14, 2010.

PCT International Search Report and Written Opinion for PCT Application No. PCT/US2009/058281, Date of Mailing Jan. 7, 2010.

PCT International Search Report and Written Opinion for PCT Application No. PCT/US2009/058285, date of mailing Apr. 14, 2010.

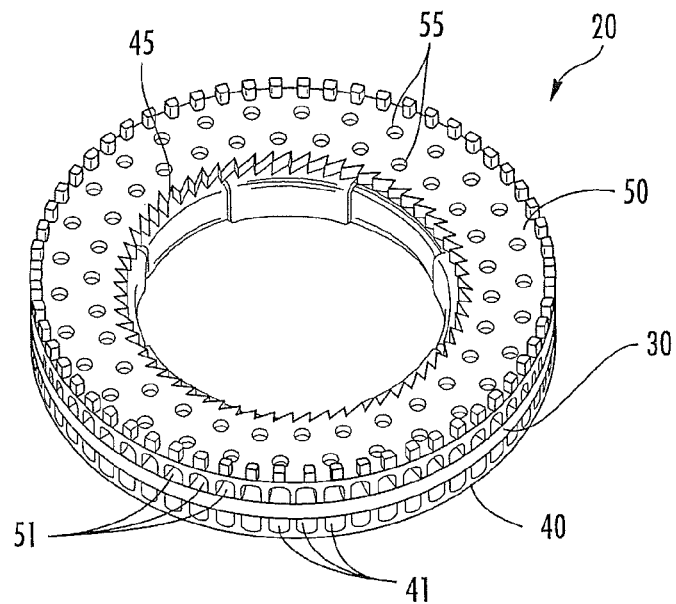
FIG. 2A
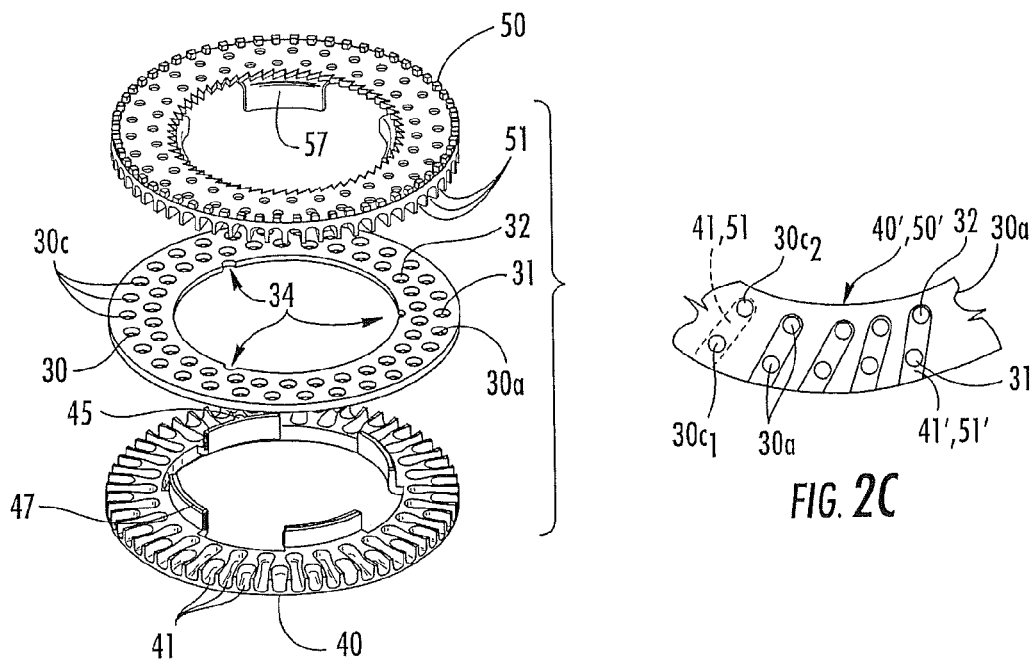
FIG. 2B
FIG. 2C

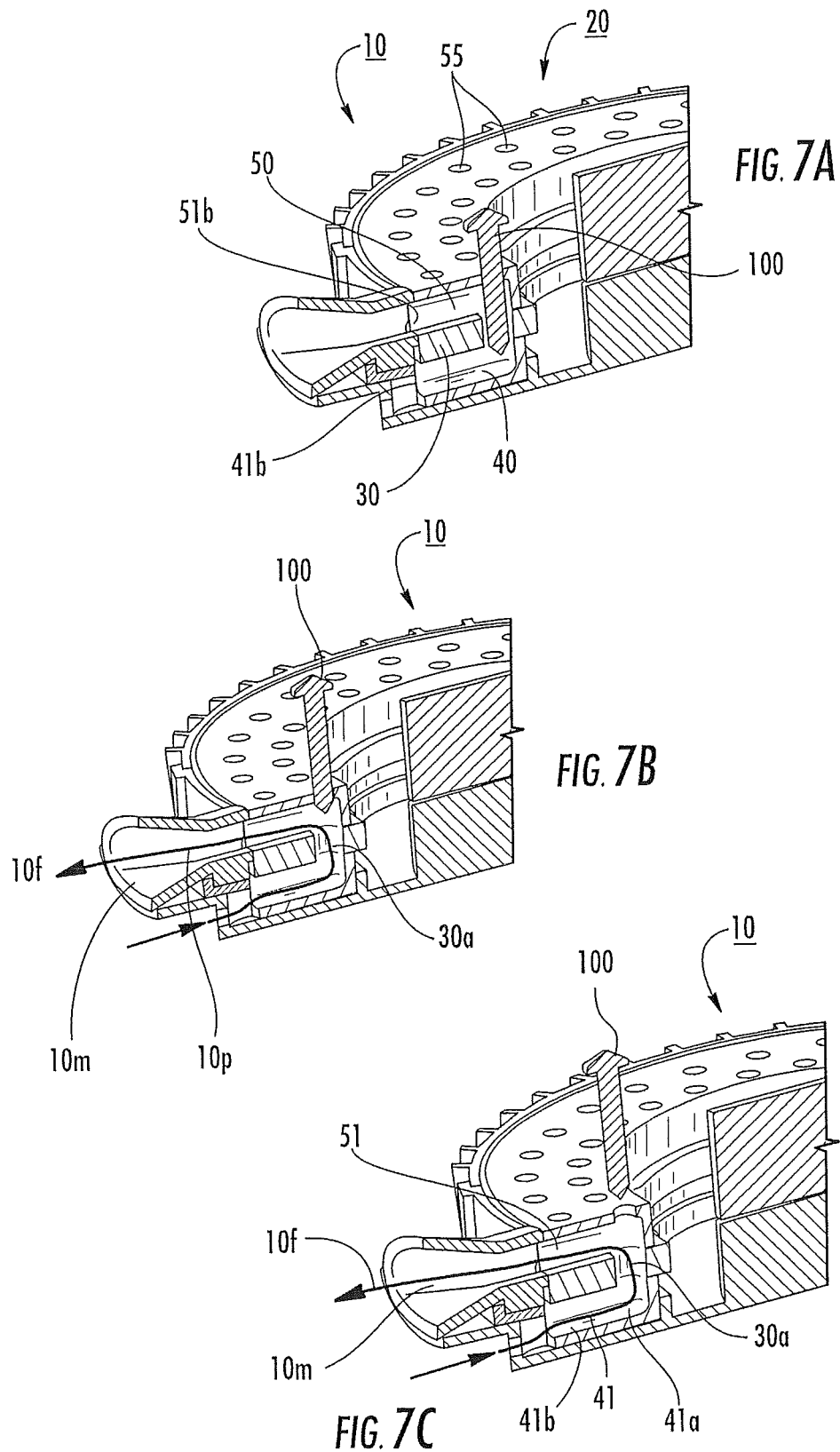

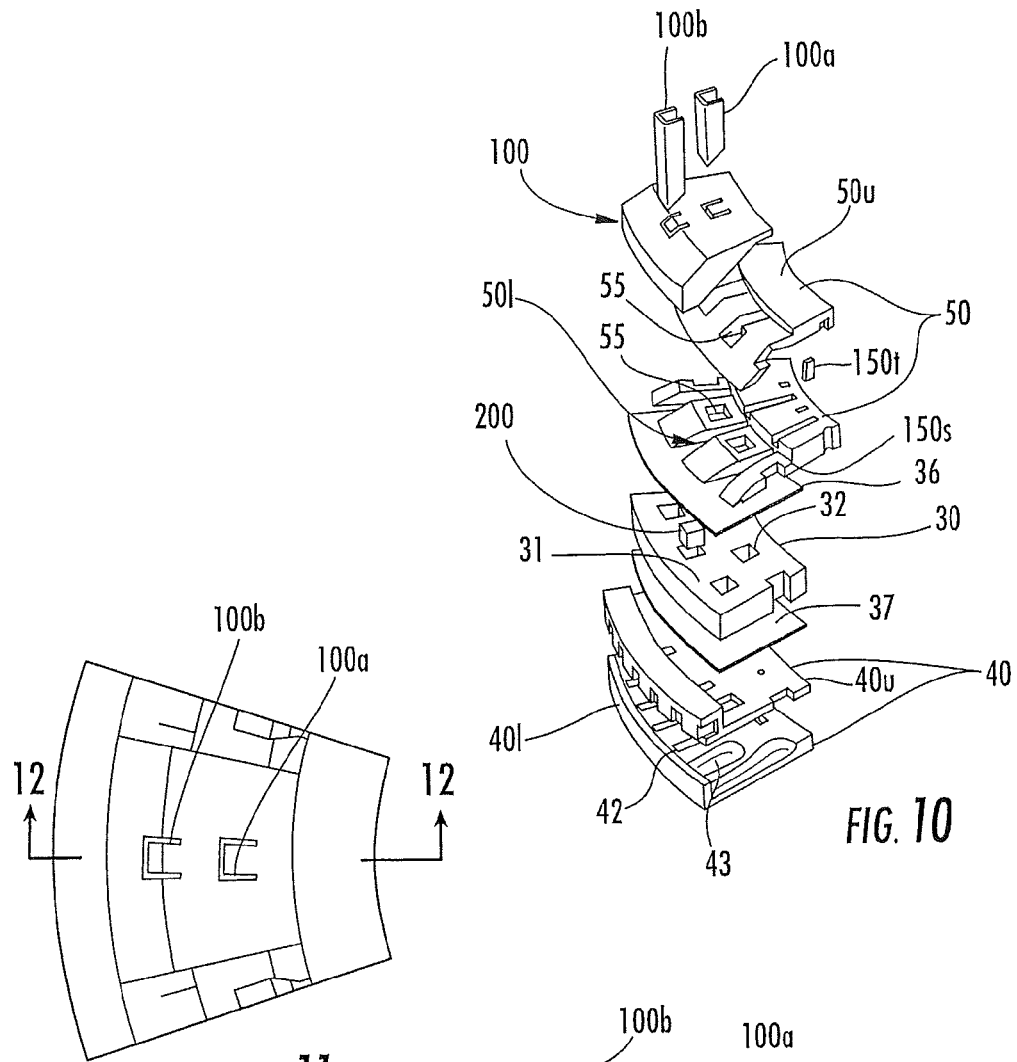
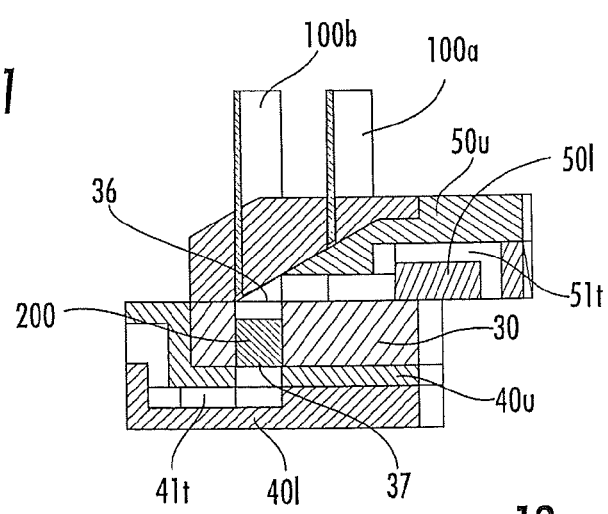
FIG. 10
FIG. 11
FIG. 12

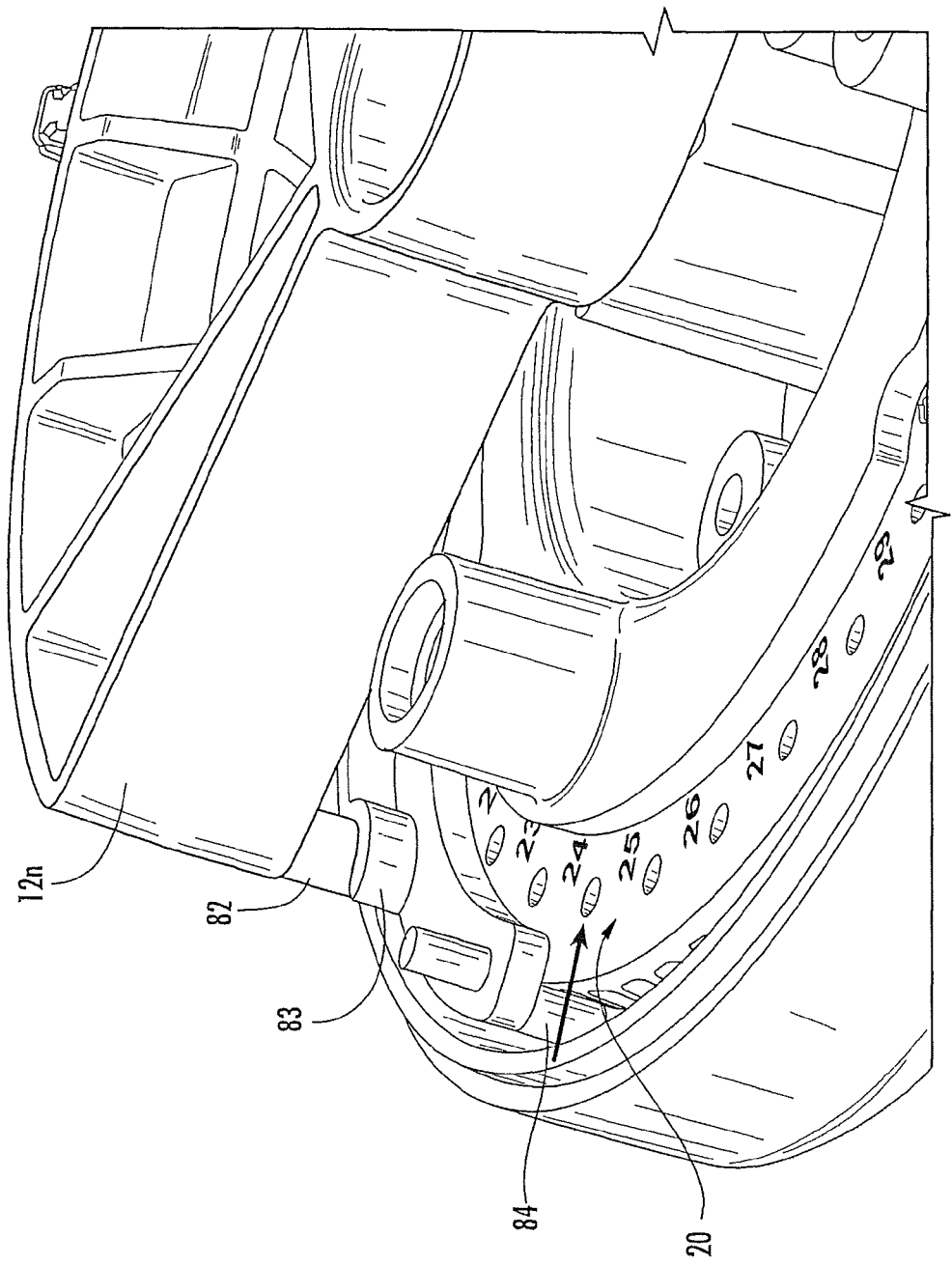

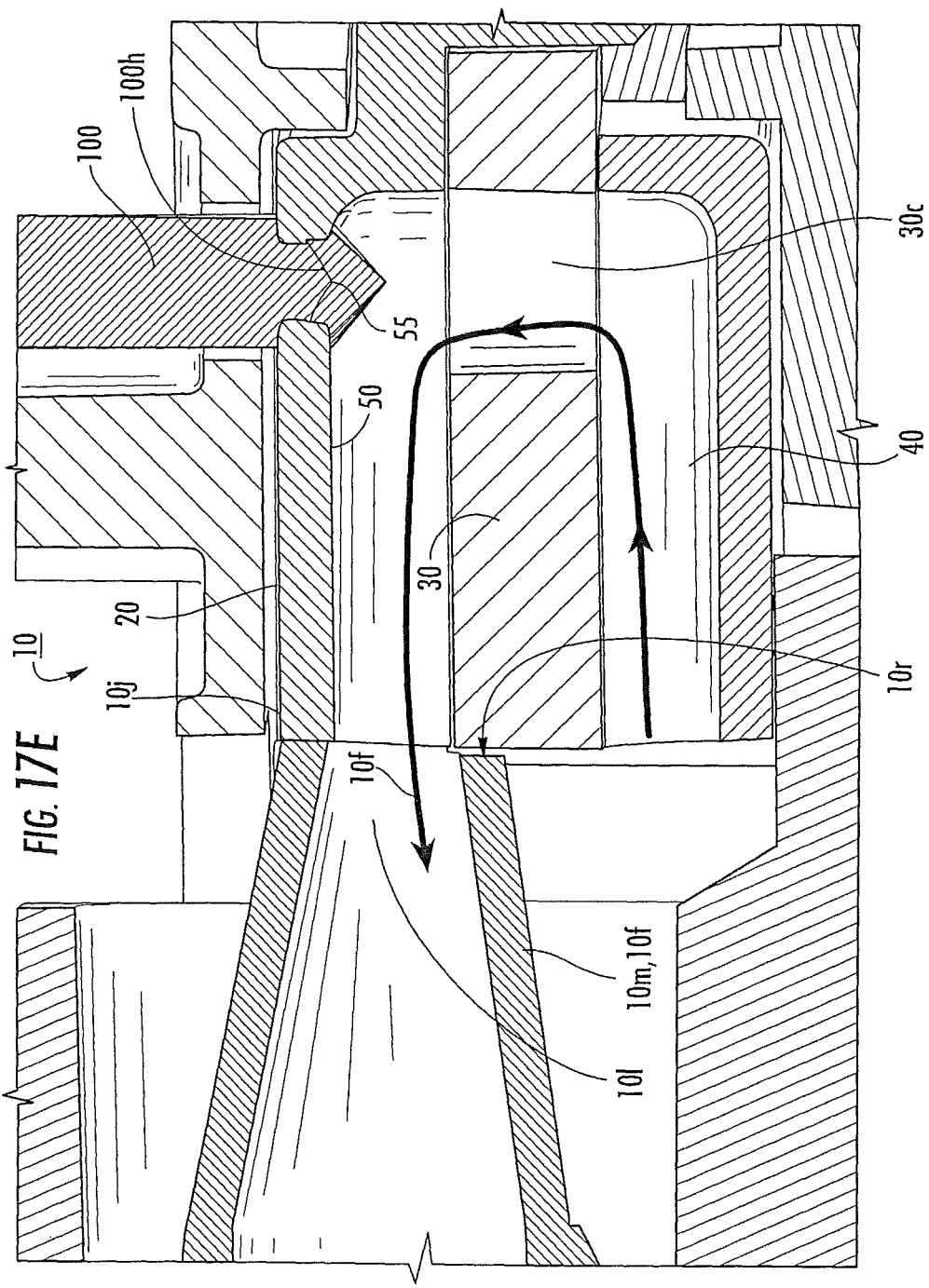

US 9,597,465 B2

METHODS OF OPERATING AND FABRICATING INHALERS WITH AIRWAY DISKS HAVING DISCRETE AIRWAY CHANNELS

RELATED APPLICATIONS

This application is a continuation application of U.S. patent application Ser. No. 13/735,532 filed Jan. 7, 2013 (and is an indirect divisional application of the parent application), which is a continuation application of U.S. patent application Ser. No. 12/566,799, filed Sep. 25, 2009, which claims the benefit of and priority to U.S. Provisional Application Ser. No. 61/100,482, filed Sep. 26, 2008, and U.S. Provisional Application Ser. No. 61/148,520, filed Jan. 30, 2009, the contents of which are hereby incorporated by reference as if recited in full herein.

FIELD OF THE INVENTION

The present invention relates to inhalers, and may be particularly suitable for dry powder inhalers.

BACKGROUND OF THE INVENTION

Generally described, known single and multiple dose Dry Powder Inhalers (DPIs) are an established alternative to pressurized metered dose inhalers (pMDIs). DPIs can use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers*, 26 Adv. Drug Delivery Rev., pp. 51-58 (1997); and Hickey et al., *A new millennium for inhaler technology*, 21 Pharm. Tech., n. 6, pp. 116-125 (1997).

In operation, DPI devices strive to administer a uniform aerosol dispersion amount in a desired physical form of the dry powder (such as a particulate size or sizes) into a patient's airway and direct it to a desired internal deposit site(s).

Unfortunately, some dry powder inhalers can retain some amount of the drug within the device that may be delivered with another dose of the drug. This may be particularly prone to happen when a user actuates the inhaler but does not inhale the indexed dose of medicament.

There remains a need for alternative inhalers and/or dose containment devices that can be used to deliver medicaments.

SUMMARY OF EMBODIMENTS OF THE INVENTION

Embodiments of the invention provide dose container assemblies that can define individual airway channels for one or more dose containers that align with an inhalation port and capture dry powder from a respective dose container(s) to define part of the inhalation path to the inhalation port for dispensing the dry powder to a user of the inhaler.

Some embodiments are directed to dry powder dose container assemblies that include: (a) a dose container disk having opposing upper and lower primary surfaces and a plurality of circumferentially spaced apart dose containers; and (b) at least one airway disk residing above or below the dose container disk. The at least one airway disk includes a plurality of circumferentially spaced apart airway channels. The dose containers can have dry powder sealed therein.

Embodiments of the invention are directed to dry powder dose container assemblies. The assemblies include: (a) a dose container disk having a plurality of circumferentially spaced apart dose containers, the dose containers having dry powder therein (typically a defined or metered amount); (b) an upper airway disk residing above the dose container disk; and (c) a lower airway disk residing below the dose container disk. The upper and the lower airway disks each include a plurality of circumferentially spaced apart channels and pairs of the lower airway disk channels and the upper airway disk channels are aligned with at least one corresponding dose container therebetween.

The dose container can be used in combination with an inhaler. The inhaler can include an inhaler body with an inhalation port and a piercing mechanism. In operation, a dose container is indexed to an inhalation position and the piercing mechanism is configured to travel through an airway disk aperture, pierce first and second sealant layers, enter, then stay or retract from the dose disk aperture while occluding the airway disk aperture, thereby allowing dry powder which falls from the dose container to reside captured in the airway channel.

In some embodiments, the dose container assembly includes both an upper and lower airway disks and each includes a respective plurality of short airway channels and a respective plurality of long airway channels, the short airway channels associated with the first row of dose container apertures and the long airway channels associated with the second row of dose container apertures. The short and long airway channels can be arranged to reside adjacent to each other and alternate circumferentially about the disk.

In some embodiments, pairs of upper and lower airway disk channels cooperate to define a curvilinear airflow path to inhibit undesired spillage of the dry powder from the inhaler (e.g., provide a sink trap configuration).

Other embodiments are directed to dry powder inhalers. The inhalers include an inhaler body with an inhalation port, a dose container assembly held in the inhaler body, a dose container opening mechanism configured to open a dose container in a dispensing position in the inhaler, and an indexing mechanism configured to rotate the dose container assembly into the dispensing position.

The dose container assembly includes a dose container disk having a plurality of circumferentially spaced apart apertures with dry powder therein. The dose container assembly also includes a lower airway disk having a plurality of airway channels with upwardly extending sidewalls residing under the dose container disk, each of the lower airway channels being in communication with at least one dose container aperture, whereby the lower airway disk channels define a plurality of spaced apart single-use or multi-use inhalation delivery paths that serially communicate with the inhalation port to thereby provide protection from inadvertent overdose.

The dose container assembly includes: (a) a dose container disk having opposing upper and lower primary surfaces and a plurality of circumferentially spaced apart apertures with first and second sealant layers attached to the upper and lower primary surfaces of the dose container disk and defining respective floors and ceilings of the dose container apertures to form dose containers holding dry powder therein; (b) an upper airway disk residing above the dose container disk, the upper airway disk comprising a plurality of circumferentially spaced apart channels with downwardly extending sidewalls; and (c) a lower airway disk residing under the dose container disk, the lower airway disk comprising a plurality of circumferentially spaced apart channels with upwardly extending sidewalls. Pairs of the lower airway disk channels and the upper airway disk channels are aligned with at least one corresponding dose container therebetween.

Yet other embodiments are directed to methods of operating an inhaler. The methods include: (a) providing a dose container ring having staggered concentric dose container apertures sealed by upper and lower sealant layers residing over and under the apertures respectively to define sealed dose containers, the dose container ring attached to an airway channel disk having a plurality of circumferentially spaced apart airway channels, at least one for each dose container; (b) rotating the dose container ring and disk together to present a respective dose container and a corresponding airway channel to a dispensing position in the inhaler; (c) advancing a piercing mechanism to open both sealant layers and release dry powder from the dose container to the corresponding airway channel; (d) leaving the piercing mechanism in an extended position or at least partially retracting the piercing mechanism; (e) fully retracting the piercing mechanism from the airway disk aperture after the step of leaving; and (f) isolating the airway channel associated with the released dry powder from an inhalation flow path so that the channel is reused only once or is not used for any subsequent inhalation delivery.

Additional embodiments are directed to methods of fabricating a dose container assembly. The methods include: (a) providing a dose container disk having upper and lower primary surfaces with a plurality of circumferentially spaced apart apertures; (b) attaching a sealant layer to one of the upper or lower primary surfaces of the dose container disk; (c) filling the dose container disk apertures with dry powder; (d) attaching a sealant layer to the other primary surface of the dose container to provide sealed dose containers; (e) placing the dose container disk between upper and lower airway disks; (f) aligning the dose containers with circumferentially spaced apart airway channels on upper and lower airway disks so that each dose container is in communication with one of the airway channels in both the upper and lower disks; and (g) attaching the upper and lower airway disks to sandwich the dose container disk therebetween.

In some embodiments, the dose container assemblies can be configured to allow for operation irrespective of orientation and to capture the dose from a respective dose container whether the inhaler device is held right side-up or down so that the dry powder is retained in the respective airway path and the inhaler is thereby resistant to overdosing. In some embodiments, the inhalers can also provide overdose protection to inhibit dispensing accumulated doses released from different dose containers.

Some embodiments are directed to dry powder dose container assemblies that include: (a) a first dose container disk having opposing upper and lower primary surfaces and a plurality of circumferentially spaced apart dose containers; (b) a second dose container disk stacked on the first dose container disk; and (c) at least one airway disk residing above or below the first or second dose container disk. The at least one airway disk includes a plurality of circumferentially spaced apart airway channels.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE FIGURES

FIG. 2A is a top perspective view of an exemplary dose container assembly according to some embodiments of the present invention.

FIG. 2B is an exploded view of the assembly shown in FIG. 2A.

FIG. 2C is a partial cutaway view of airway channels aligned with two dose containers according to some embodiments of the present invention.

FIGS. 7A-7C are partial cutaway views of a dose container assembly in an inhaler cooperating with a piercing mechanism having a three-stage operation sequence according to some embodiments of the present invention.

FIG. 10 is a partial exploded view of the device shown in FIG. 9A according to some embodiments of the present invention.

FIG. 11 is a top assembled view of the portion of the device shown in FIG. 10.

FIG. 12 is a side section view taken along lines 12-12 of FIG. 11, illustrating an outer ring actuation according to some embodiments of the present invention.

FIGS. 17B-17D are greatly enlarged partial cutaway side perspective views of an inhaler with a biasing mechanism according to embodiments of the present invention.

FIG. 17E is a greatly enlarged cutaway view of an airflow path in an inhaler and secure airpath joint provided by a biasing mechanism such as that shown, for example, in FIG. 17B-17D or 17F and 17G according to embodiments of the present invention.

DESCRIPTION OF EMBODIMENTS OF THE INVENTION

Figure 1A:
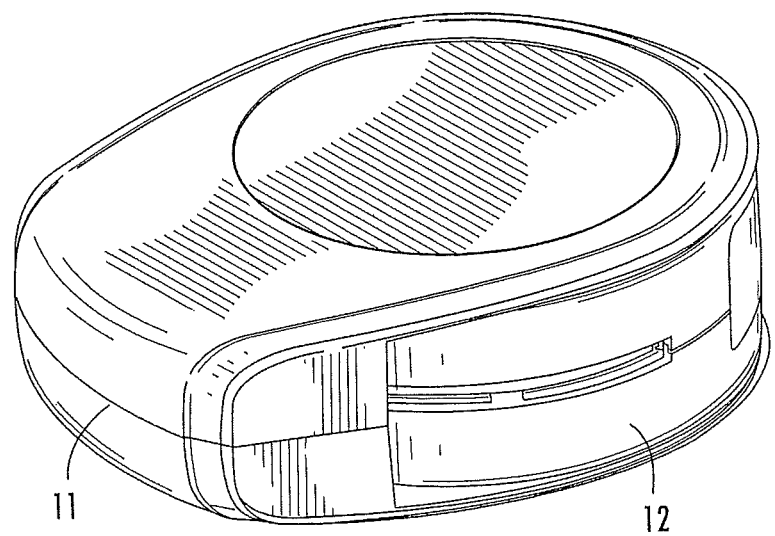
FIG. 1A is a front perspective view of an inhaler with a cover according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms "first" and "second" are used herein to describe various components, regions, layers and/or sections, these regions, layers and/or sections should not be limited by these terms. These terms are only used to distinguish one component, region, layer or section from another component, region, layer or section. Thus, a first component, region, layer or section discussed below could be termed a second component, region, layer or section, and vice versa, without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the description of the present invention that follows, certain terms are employed to refer to the positional relationship of certain structures relative to other structures. As used herein, the term "front" or "forward" and derivatives thereof refer to the general or primary direction that the dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "deagglomeration" and its derivatives refer to flowing or processing dry powder in the inhaler airflow path to inhibit the dry powder from remaining or becoming agglomerated or cohesive during inspiration.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery, but are typically oral inhalers.

The terms "sealant", "sealant layer" and/or "sealant material" includes configurations that have at least one layer of at least one material and can be provided as a continuous layer that covers the entire upper surface and/or lower surface or may be provided as strips or pieces to cover portions of the device, e.g., to reside over at least a target one or more of the dose container apertures. Thus, terms "sealant" and "sealant layer" includes single and multiple layer materials, typically comprising at least one foil layer. The sealant or sealant layer can be a thin multi-layer laminated sealant material with elastomeric and foil materials. The sealant layer can be selected to provide drug stability as they may contact the dry powder in the respective dose containers.

The sealed dose containers can be configured to inhibit oxygen and moisture penetration to provide a sufficient shelf life.

The term "primary surface" refers to a surface that has a greater area than another surface and the primary surface can be substantially planar or may be otherwise configured. For example, a primary surface can include protrusions or recessions, such as where some blister configurations are used. Thus, a disk can have upper and lower primary surfaces and a minor surface (e.g., a wall with a thickness) that extends between and connects the two.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents, agents or ingredients with one or a plurality of (average) particulate size ranges. The term "low-density" dry powder means dry powders having a density of about 0.8 $g/cm^3$ or less. In particular embodiments, the low-density powder may have a density of about 0.5 $g/cm^3$ or less. The dry powder may be a dry powder with cohesive or agglomeration tendencies.

The term "filling" means providing a bolus or sub-bolus metered amount of dry powder. Thus, the respective dose container is not required to be volumetrically full.

In any event, individual dispensable quantities of dry powder formulations can comprise a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50

μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroids, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, anti-androgenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). The dose amounts and type of drug held by a dose container system may vary per dose container or may be the same. In some embodiments, the dry powder dose amounts can be about 100 mg or less, typically less than 50 mg, and more typically between about 0.1 mg to about 30 mg.

In some embodiments, such as for pulmonary conditions (i.e., asthma or COPD), the dry powder can be provided as about 5 mg total weight (the dose amount may be blended to provide this weight). A conventional exemplary dry powder dose amount for an average adult is less than about 50 mg, typically between about 10-30 mg and for an average adolescent pediatric subject is typically from about 5-10 mg. A typical dose concentration may be between about 1-5%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during inhalation, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective drug compartment or dose container is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a dose container/drug compartment in a "compressed" or partially compressed manner or may be provided as free flowing particulates.

Some embodiments of the invention are directed to inhalers that can deliver multiple different drugs for combination delivery. Thus, for example, in some embodiments, some or all of the dose containers may include two different drugs or different dose containers may contain different drugs configured for dispensing substantially concurrently.

The inhalers can be configured to provide any suitable number of doses, typically between about 30-120 doses, and more typically between about 30-60 doses. The inhalers can deliver one drug or a combination of drugs. In some embodiments, the inhalers can provide between about 30-60 doses of two different drugs (in the same or different unit amounts), for a total of between about 60-120 individual unit doses, respectively. The inhaler can provide between a 30 day to a 60 day (or even greater) supply of medicine. In some embodiments, the inhalers can be configured to hold about 60 doses of the same drug or drug combination, in the same or different unit amounts, which can be a 30 day supply (for a twice per day dosing) or a 60 day supply for single daily treatments.

Certain embodiments may be particularly suitable for dispensing medication to respiratory patients, diabetic patients, cystic fibrosis patients, or for treating pain. The inhalers may also be used to dispense narcotics, hormones and/or infertility treatments.

The dose container assembly and inhaler may be particularly suitable for dispensing medicament for the treatment of respiratory disorders. Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person of skill in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Some particular embodiments of the dose container assembly and/or inhaler include medicaments that are selected from the group consisting of: albuterol, salmeterol, fluticasone propionate and beclometasone dipropionate and salts or solvates thereof, e.g., the sulphate of albuterol and the xinafoate of salmeterol. Medicaments can also be delivered in combinations. Examples of particular formulations containing combinations of active ingredients include those that contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Figure 1B:
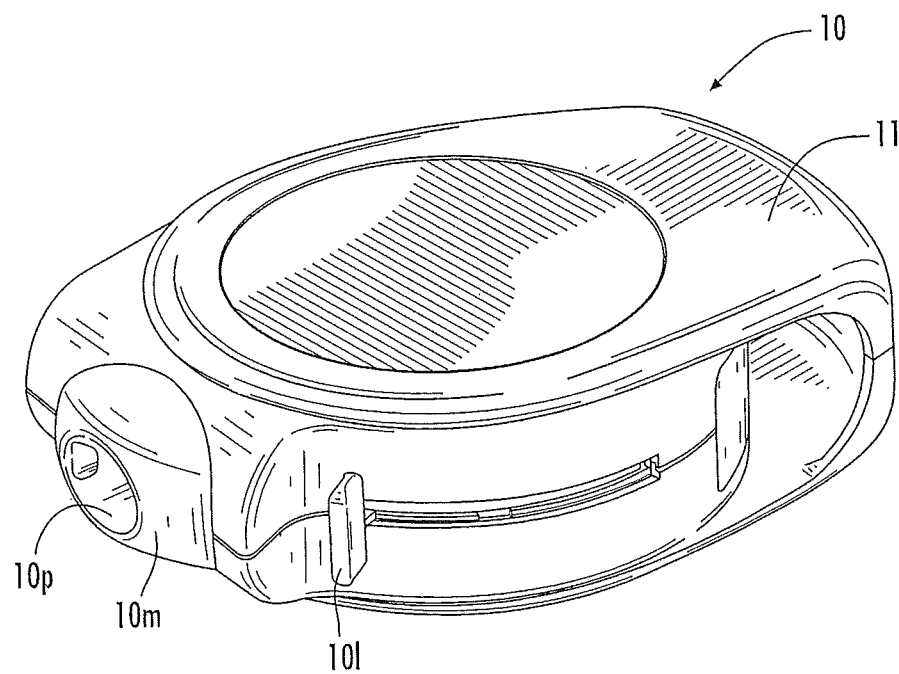
FIG. 1B is a front perspective of the inhaler shown in FIG. 1A with the cover in an open position according to some embodiments of the present invention.

Turning now to the figures, FIGS. 1A and 1B illustrate an example of a multi-dose inhaler 10 with a cover 11 and inhalation port 10p. The cover 11 may extend over a top surface of the inhaler to extend down over an inhalation port 10p of the mouthpiece 10m, then extend rearward away from the mouthpiece 10m over a bottom surface of the inhaler. However, this inhaler configuration is shown merely for completeness and embodiments of the invention are not limited to this inhaler configuration as other form factors, covers and inhalation port configurations may be used.

FIG. 2A illustrates a dose container assembly 20 with a dose ring or disk 30 having a plurality of dose containers 30c. As shown in FIGS. 2B and 2E, in some embodiments, the dose ring or disk 30 can include a plurality of circumferentially spaced apart through apertures 30a that form a portion of the dose containers 30c. As shown in FIG. 2E, the dose containers 30c can be defined by dose container apertures 30a and upper and lower sealants 36, 37.

As shown, the dose container assembly 20 includes a lower airway disk 40 and an upper airway disk 50. In other embodiments, the dose container assembly 20 can include the dose container disk 30 and only one of the lower airway disk 40 or the upper airway disk 50. In such a configuration, another type of airway can be used for the other side of the disk 30, such as, but not limited to, a fixed or "global" upper or lower airway can be used with the individual airways provided by either an upper or lower airway disk 50, 40. Also, it is contemplated that the upper and lower airway disks 50, 40 described herein can be reversed for normal operation (or inadvertently for atypical operation) so that the lower airway disk is the upper airway disk and the upper airway disk is the lower airway disk.

As shown in FIGS. 2A and 2B, the lower and upper airway disks 40, 50, respectively, include a plurality of circumferentially spaced apart airway channels 41, 51, respectively. Typically, the disks 40, 50 include one channel 41, 51 for one dose container 30c. However, in other embodiments, as shown, for example, in FIG. 2C, a respective airway channel 51, 41 from one or both of the disks 50', 40' can be in communication with two or more different dose containers 30c. This configuration will allow for (simultaneous) combination delivery of two or more different dry powders from two or more dose containers 30c in communication with the associated one airway channel 51 or 41 and/or a respective airway channel pair. Thus, while embodiments of the invention are illustrated as releasing only a dose from a single dose container 30c during one delivery, other embodiments allow the inhalers to dispense a combination drug so that two or more dose containers 30c may use a respective airway channel 41, 51 for delivery.

Figure 2D:
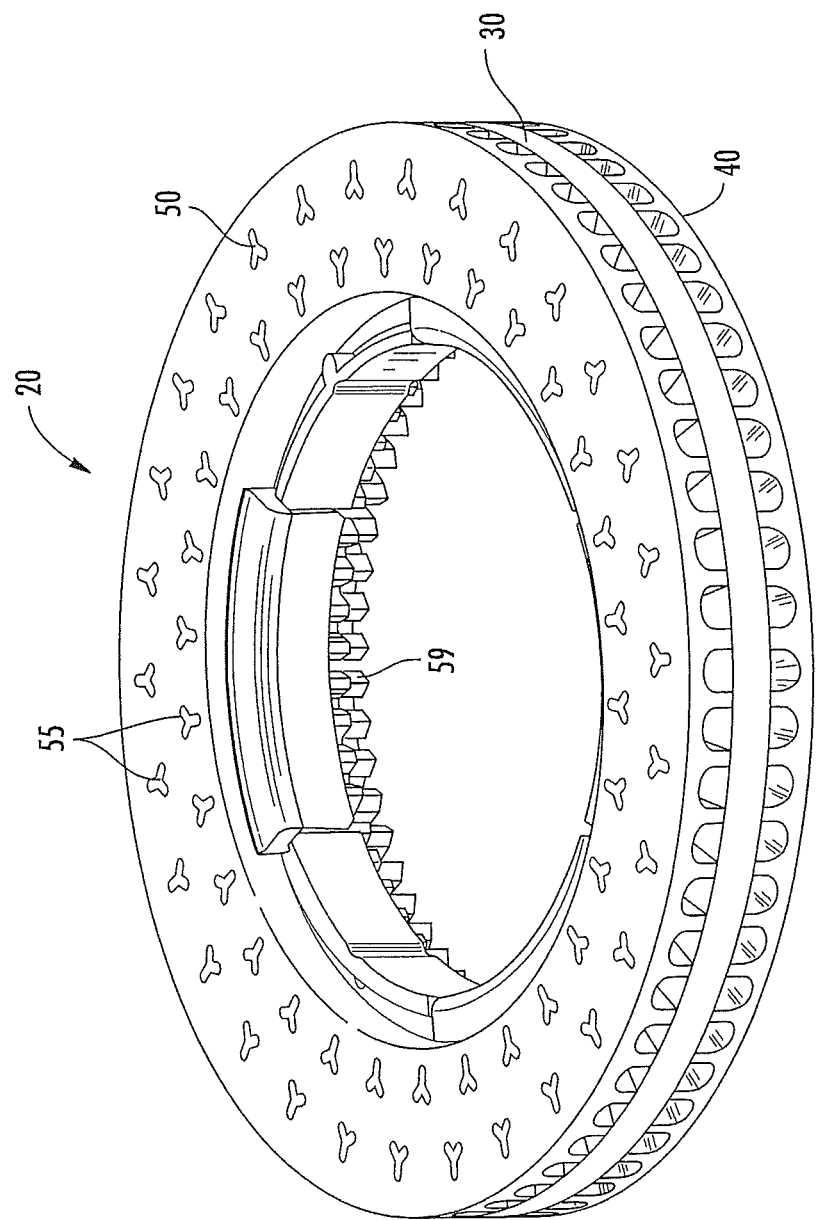
FIG. 2D is a top perspective view of another exemplary dose container assembly according to some embodiments of the present invention.
Figure 2E:
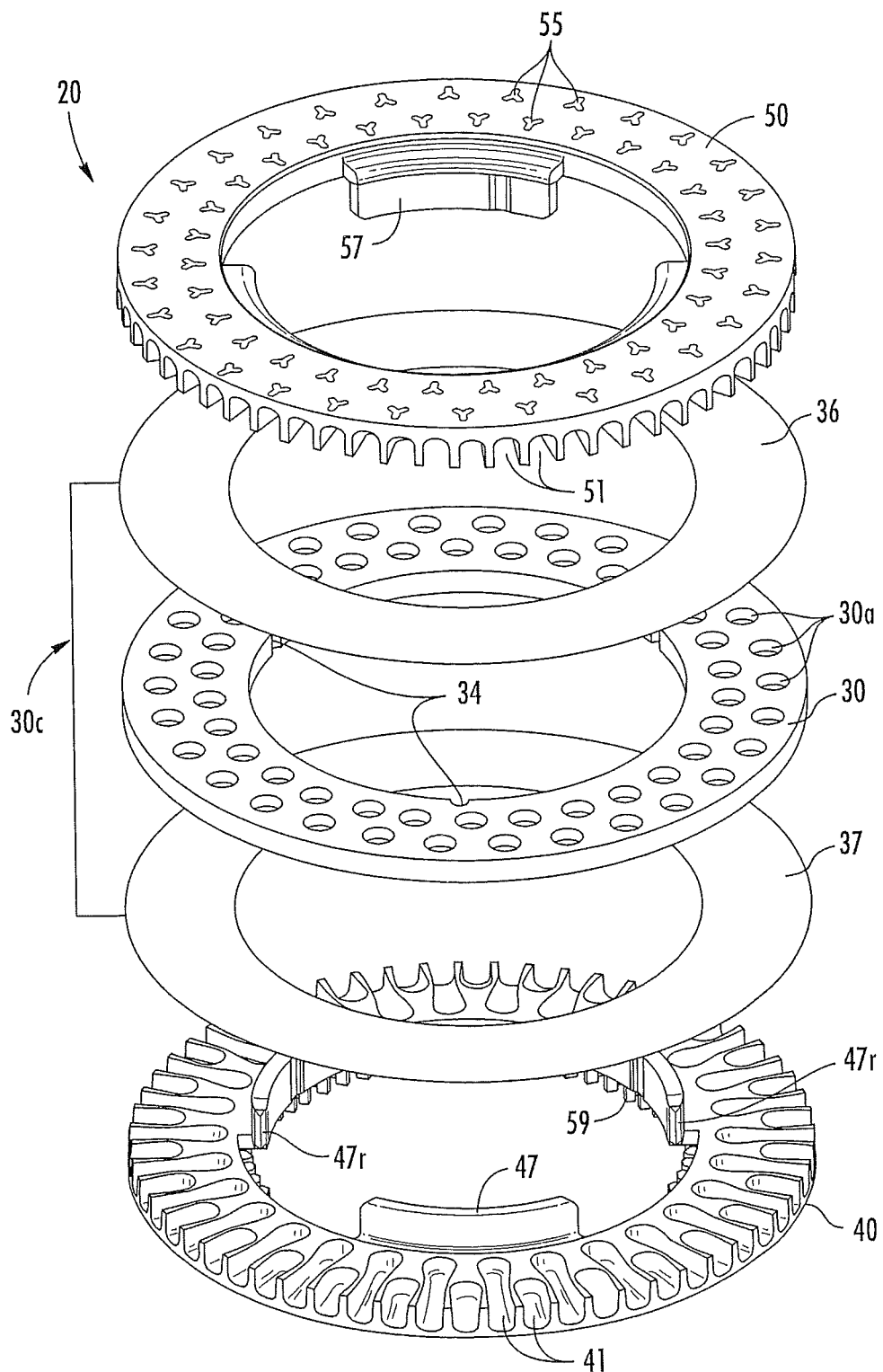
FIG. 2E is an exploded view of the dose container assembly shown in FIG. 2D according to embodiments of the present invention.

It is also noted that the disk 30 can have a single dose container 30c circumferentially located between aligned dual containers $30c_1$, $30c_2$. However, in other embodiments, the dose disk 30 can also be configured so that the dose disk 30 has radially spaced apart dual (or more) containers $30c_1$, $30c_2$ with a corresponding airway channel 41/51 (typically a channel pair) and does not require either the shorter channels 41, 51 or the single dose containers 30c. The dose containers can be arranged in concentric rows of aligned pairs (or more) of dose containers. In some embodiments, the combination delivery configuration can employ dose containers $30c_1$, $30c_2$ which can be configured to reside under or over a respective airway channel 41/51, but the airway channel 41/51 can angularly extend from a dose container proximate the inner perimeter to a staggered dose container proximate the outer perimeter of the disk as shown in FIG. 2G. However, the airway channel(s) can extend over or under two or more dose channels with non-staggered centerlines.

Figure 2F:
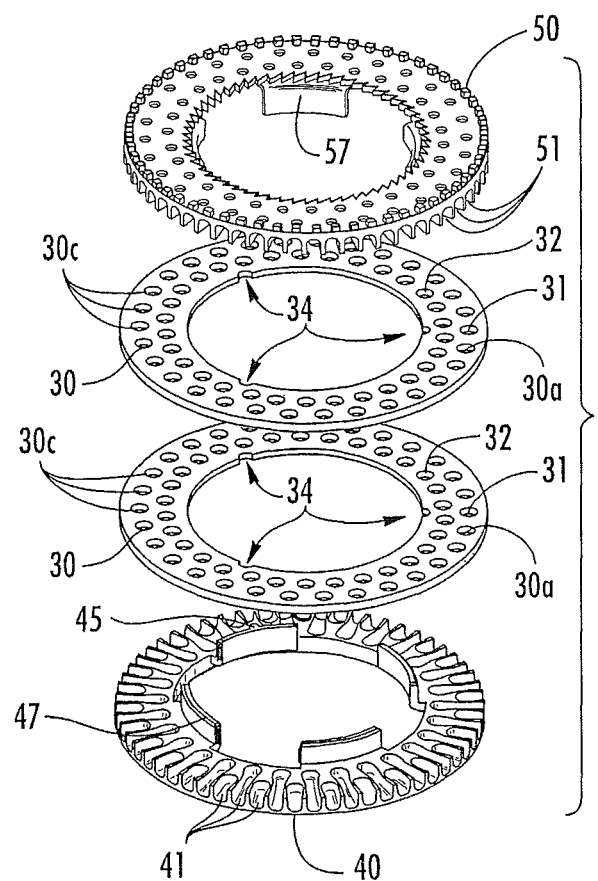
FIG. 2F is an exploded view of a dose container assembly with stacked dose disks according to embodiments of the present invention.
Figure 2G:
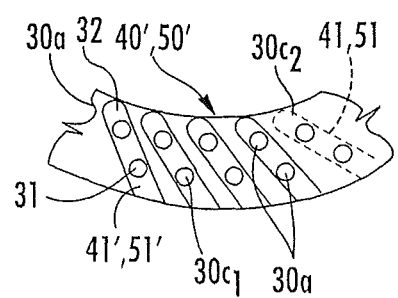
FIG. 2G is a partial cutaway view of airway channels aligned with two concentric rows of staggered dose containers according to some embodiments of the present invention.

In other embodiments, as shown in FIG. 2F, two or more dose disks 30 can be stacked and reside either sandwiched between the airway channel disks 40, 50 or can be used with a single airway disk 40/50 and the piercer can be configured to open two or more stacked dose disk containers to release the medicaments from two or more stacked dose containers and allow inhalation using one or both channels 41, 51.

In other embodiments, the different dose containers in communication with the respective airway channel 51, 41 can allow one dose container $30c_1$ to release dry powder to the airway channel 41 and/or 51, then be used again later for another dose container $30c_2$. Thus, embodiments of the invention allow for some or all airway channels 41, 51 to be used once or twice (although other configurations may allow for greater number of uses).

In some embodiments, the airway channels 41, 51 can define airways that are not able to release dry powder residing in a respective airway channel to a user once the inhaler is indexed again to another position so that the outer ring of dose containers are aligned with airway disks. The channels can be configured to have "sink traps" to inhibit spillage according to some embodiments of the present invention to provide overdose protection (unless the dual use configuration is used whereby only a single other dose may be released using that airway channel(s) as noted above).

Where two airway disks are used, e.g., both the lower and upper disks 40, 50, the inhaler device 10 can be configured to operate even when inverted and have the same overdose protection feature. Spillage of dry powder from the inhaler 10 as the dose container 30c is opened can be influenced by gravity. For example, for a conventional obround or elliptical mouthpiece shape, there are two primary device orientations (right-side-up and upside-down), embodiments of the invention allow for operation of the inhaler device in both orientations. In the embodiment shown, for example, in FIG. 2A, this can be accomplished by having an individual airway section for a respective dose container 30c (or dose containers where combination drug delivery is desired) both above and below the target corresponding dose container(s) 30c.

Figure 3A:
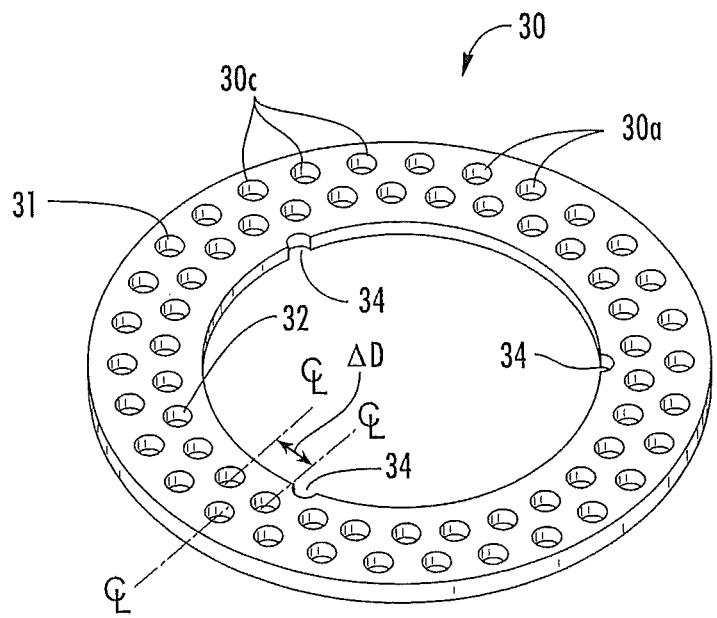
FIG. 3A is a top perspective view of a dose container ring according to some embodiments of the present invention.
Figure 3B:
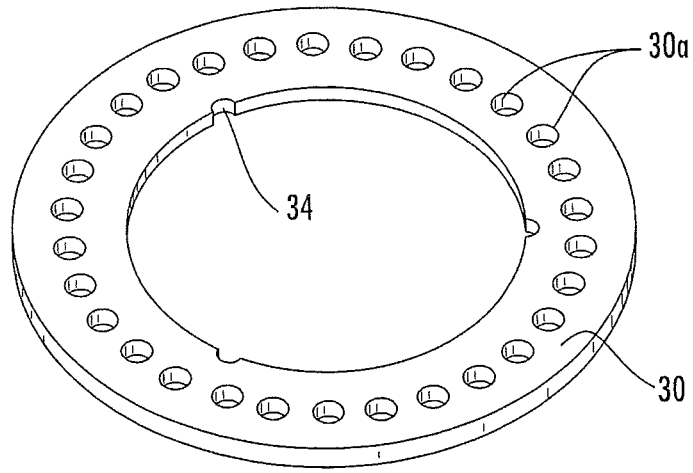
FIG. 3B is a top perspective view of a dose container ring according to some other embodiments of the present invention.

FIGS. 2A, 2D and 3A illustrate that the dose container disk 30 can include 60 dose containers 30c while FIG. 3B illustrates that the dose container disk 30 can include 30 dose containers 30c. Greater or lesser numbers of dose containers may be used.

FIG. 2E illustrates that sealant layers 36, 37 may be configured as annular flat rings as shown can be used to seal the top and bottom surfaces of the dose disk 30. The sealant layers 36, 37 can have the same or different material(s) and may include foil, polymer(s) and/or elastomer(s), or other suitable material or combinations of materials, including laminates. Typically, the sealant layers 36, 37 are thin flexible sealant layers comprising foil.

Figure 17A:
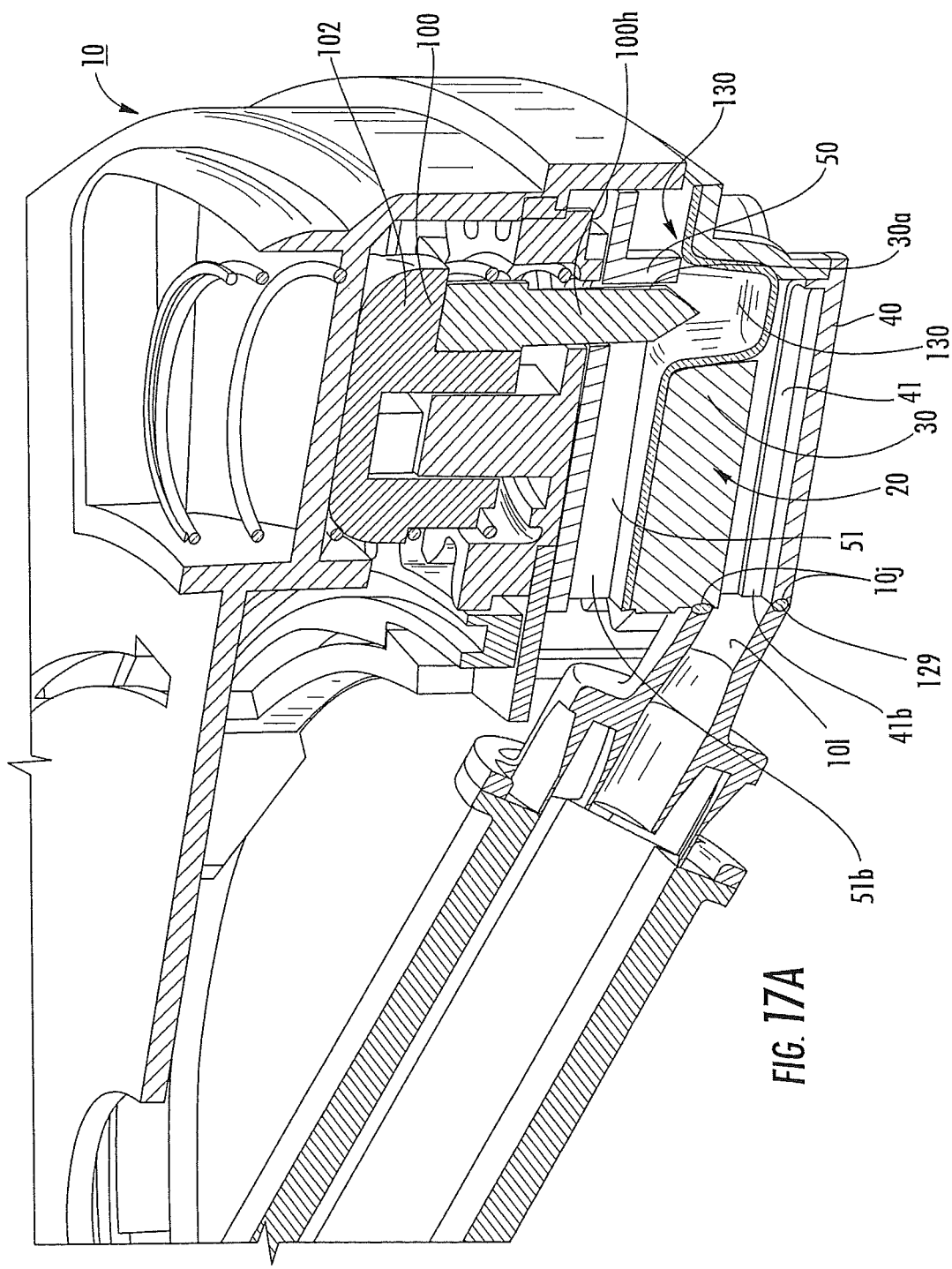
FIG. 17A is a greatly enlarged partial cutaway view of an inhaler with discrete airway channels for each dose container and a long airway path according to some embodiments of the present invention.

The sealant layers 36, 37 (where used) may be provided as a substantially continuous ring as shown in FIG. 2E or may be attached to the dose container disk 30 as individual strips or spots of sealant that can be placed over and under the apertures 30a. In other embodiments, sealant layers may be provided on only one primary surface of the dose disk 30, and the apertures 30a may be closed on one side rather than have through apertures (not shown). In yet other embodiments, the dose disk 30 can have a blister configuration 130 (FIG. 17A).

FIGS. 2A, 2D, 3A and 3B also illustrate that the dose container disk 30 can include at least one indexing notch 34, shown as a plurality of circumferentially spaced apart indexing notches 34. A mating component on one of the other disks 40, 50 can be used to help orient the disks 30, 40, 50 relative to each other. For example, one of the airway disks 40, 50, typically the lower disk 40, may include an inner wall with an outwardly radially extending tab 45 (FIGS. 4A, 6) that aligns with and engages one of those notches 34 to position the channels 41, 51 in alignment with the dose containers 30c. Other alignment means may be used, including, for example, the reverse of the notch and tab configuration described (e.g., one or both airway disks 40, 50 can have a notch and the dose container disk 30 can include a tab or other component).

As shown in FIGS. 2B, 2D, 3A and 3B, the dose containers 30c may be arranged so that they are circumferentially spaced apart in one or more rows. As shown in FIG. 3A, the dose containers 30c are arranged in staggered concentric rows, a front row 31 at a first radius from a center of the disk and a back row 32 at a second different radius. The dose containers 30c can be arranged so that centerlines of the dose containers 30c of the back row are circumferentially offset from the centerlines of the dose containers 30c in the front row by a distance. As shown in FIG. 3A dose containers 30c on each respective row are spaced apart a distance "D" and the offset of the centerlines of those on the back row to those on the front row is "D/2". The dose container disk 30 can be a molded polymer, copolymer or blends and derivatives thereof, or may comprise metal, or combinations thereof, or other materials that are capable of providing sufficient moisture resistance.

The dose container disk 30 can have an outer diameter of between about 50-100 mm, typically about 65 mm and a thickness of between about 2-5 mm, typically about 3 mm. The disk 30 can comprise a cyclic olefin (COC) copolymer. The apertures 30a can have a diameter of between about 2-5 mm, typically about 3 mm and the sidewalls 30w of the dose containers 30c may have an angle or draft of about 1-3 degrees per side, typically about 1.5 degrees, as shown in FIG. 3D, to facilitate removal from a mold (where a molding process is used to form the disk 30). The dose container 30 is configured to be able to protect the powder from moisture ingress, while providing a desired number of doses in a compact overall inhaler size. The individual dose container apertures 30a are spaced apart from each other to allow sufficient seal area and material thickness for moisture protection of the powder.

Figure 3C:
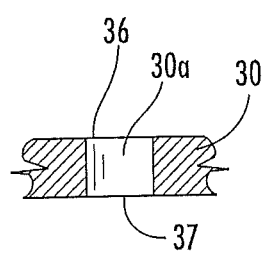
FIG. 3C is a partial cutaway view of a single dose container according to some embodiments of the present invention.
Figure 3D:
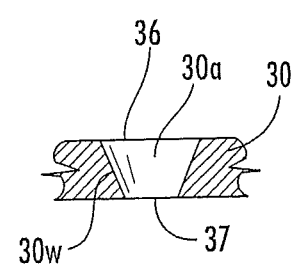
FIG. 3D is a partial cutaway view of a single dose container according to some embodiments of the present invention.

Similar to the embodiment shown in FIG. 2E, FIG. 3C illustrates that the dose containers 30c may be defined by apertures 30a sealed by sealant layers 36, 37 over and under the apertures 30a. As discussed above, the sealant layers 36, 37 can include foil, a polymer and/or elastomer, or other suitable materials or combinations of materials, including laminates. In a dry powder medicament inhaler 10, the drug powder is stored in a closed, moisture-resistant space provided by the dose containers 30c.

Embodiments of the invention provide a dose container assembly 20 that can provide a suitable seal and facilitate attachment of the airway disks 40, 50 to hold the dose ring or disk 30 therebetween. As shown in FIGS. 2D, 2E, in some embodiments, the dose container disk 30 contains sealants 36, 37 which may be a continuous layer over the upper and lower (primary) surfaces of the dose disk 30 and the upper and lower airway disks 50, 40 can contact the respective sealant and abut the dose disk 20 to allow for a tight fit. The exemplary attachment features shown in FIGS. 2A, 2E and 6 can reduce air leakage by allowing a close fit of the airway disks 40, 50 to the dose ring 30. The disks 40, 50 can sandwich the dose ring 30 and the dose ring can act as the "stop" to set the depth of engagement of the assembly features on the airway disks 40, 50. Embodiments of the invention provide a feature to index and/or orient the airway disks 40, 50 relative to the dose ring 30 as discussed above. In addition or alternatively, as shown in FIGS. 2E and 4A, in some embodiments, relatively simple frictional engagement members, such as, but not limited to, "crush ribs" 47r, on one or both of the airway disks 40, 50 may be used to secure their attachment to each other as will be discussed further below.

Figure 4A:
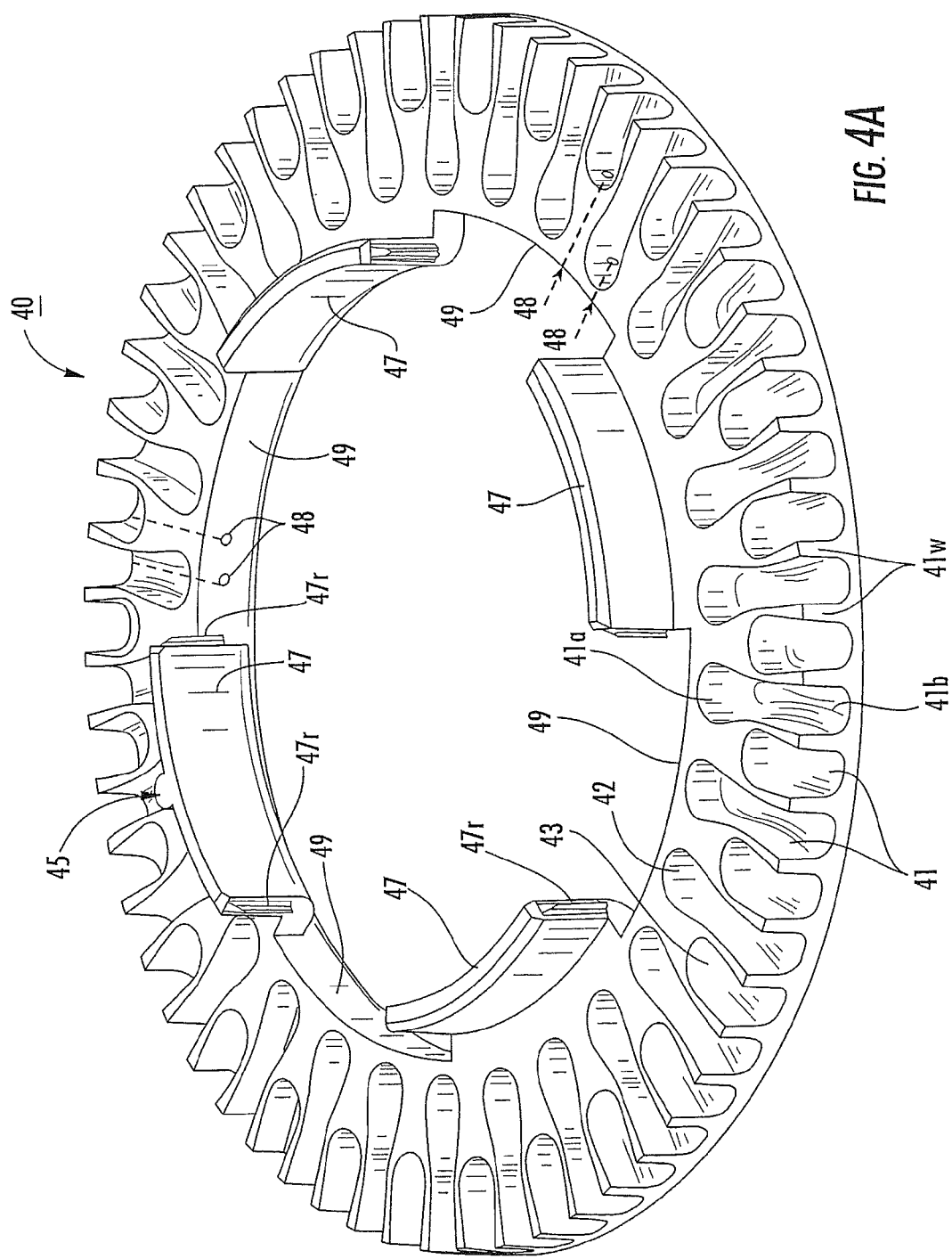
FIG. 4A is a greatly enlarged top perspective view of a lower airway disk according to some embodiments of the present invention.

FIG. 4A illustrates an example of a lower airway disk 40. As shown, the disk 40 defines a plurality of circumferentially spaced apart channels 41. For the staggered concentric dose container configuration, the disk 40 can include alternating long and short airway channels 42, 43, respectively. Each channel 41 includes opposing end portions 41a, 41b, one (substantially or entirely) closed end portion 41a typically positioned adjacent the dose container 30c and one open end portion end portion 41b. The open end portion end portion 41b can merge into and/or is positioned adjacent the exit port 10p and/or mouthpiece 10m (FIGS. 7A-7C) and/or a make-up air port or channel. The intake and flow can be in either direction and the open end 41b can be configured to face either the inner or outer perimeter of the disk 40 (e.g., be either positioned radially innermost or radially outermost on the disk 40). The channels 41 include upwardly extending sidewalls 41w with adjacent pairs of the long and short channels sharing one of the sidewalls 41w. Optionally, as shown by feature 48 in FIG. 4A aligned with some channels, all or some of the channels 41 can include a small bleed hole 48 that allows air to enter but is sized to inhibit dry powder from exiting therefrom (the bleed holes 48 are shown only with a few of the channels 41 for ease of illustration).

Figure 4B:
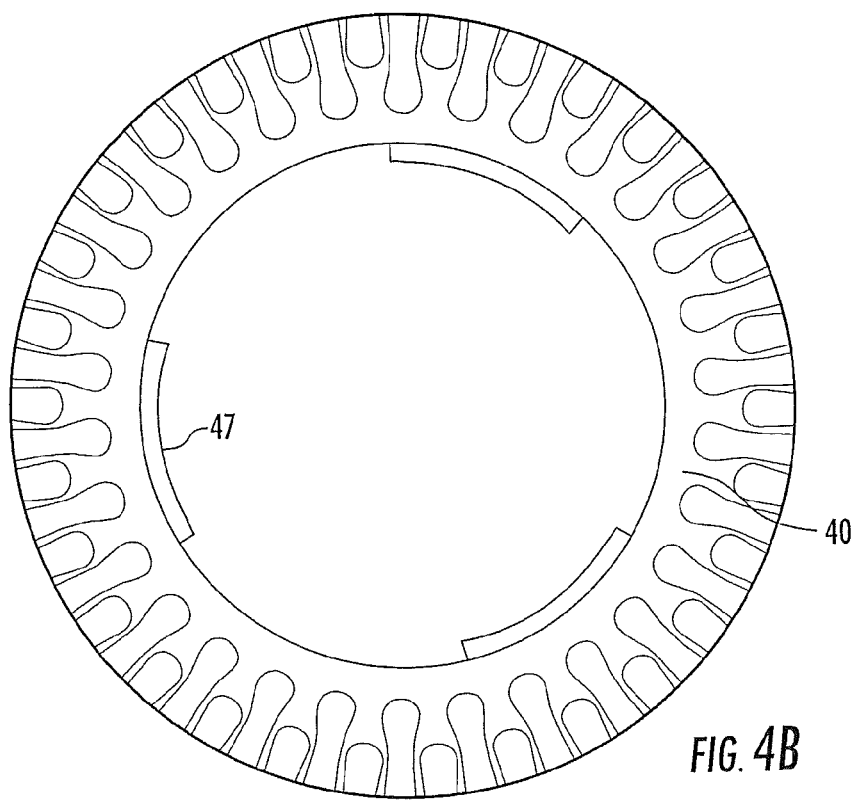
FIG. 4B is a top view of a lower airway disk according to some embodiments of the present invention.

FIGS. 4A and 4B also illustrate that the disk 40 can include circumferentially spaced apart upwardly extending walls or tabs 47. One of which can include the radially (outwardly) extending tab 45 discussed above. The disk 40 can also or alternatively optionally include circumferentially extending recesses which align with tabs on the upper airway disk 50 to sandwich the dose disk 30 therebetween. The tabs 47 can optionally include crush ribs 47r that matably engage with tabs 57 on the upper airway disk 50 to hold the three piece dose disk assembly 20 together with sufficient force without requiring and additional attachment means.

Figure 4C:
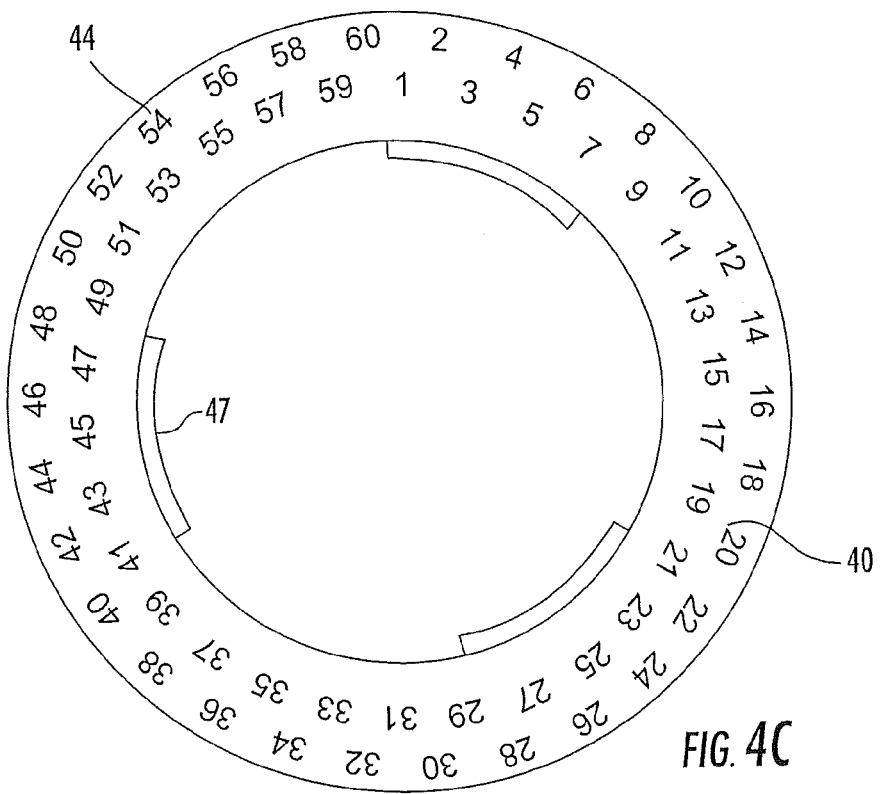
FIG. 4C is a bottom view of an exemplary lower airway disk.
Figure 18A:
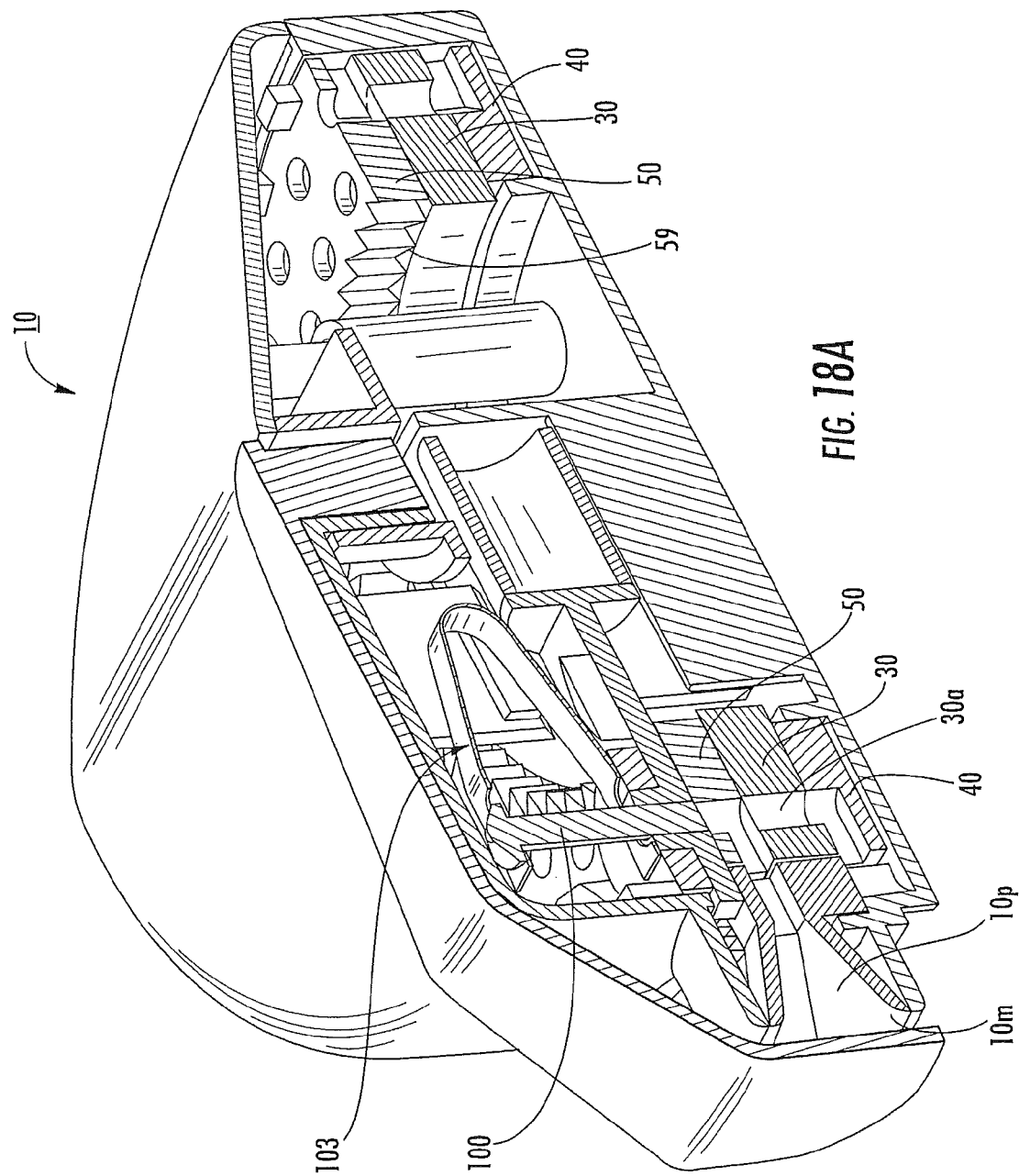
FIG. 18A is a greatly enlarged partial cutaway view of an inhaler with discrete airway channels and a short airway path according to some embodiments of the present invention.
Figure 18B:
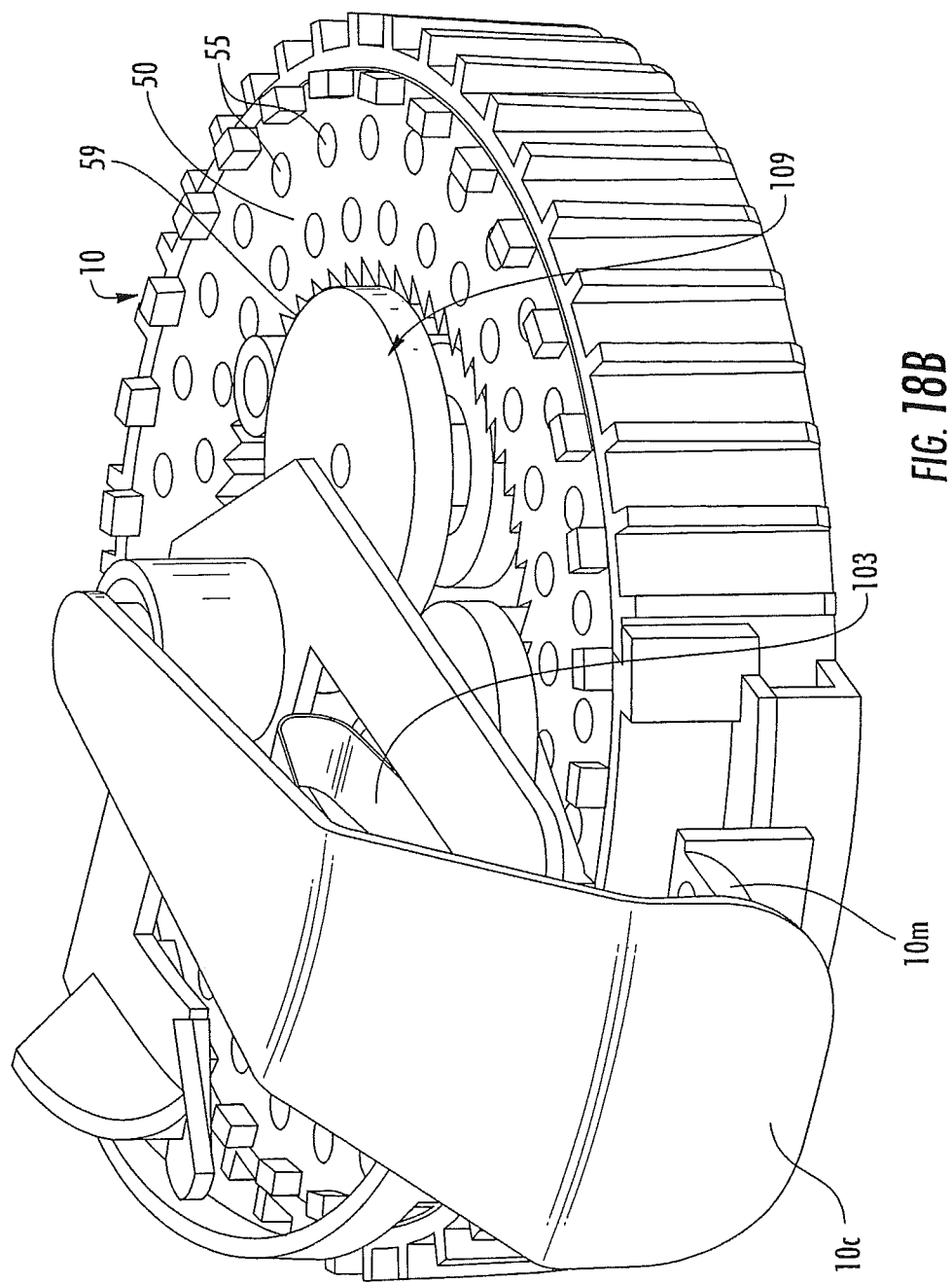
FIG. 18B is a greatly enlarged partial cutaway view of the inhaler shown in FIG. 18A illustrating an indexing mechanism according to some embodiments of the present invention.
Figure 18C:
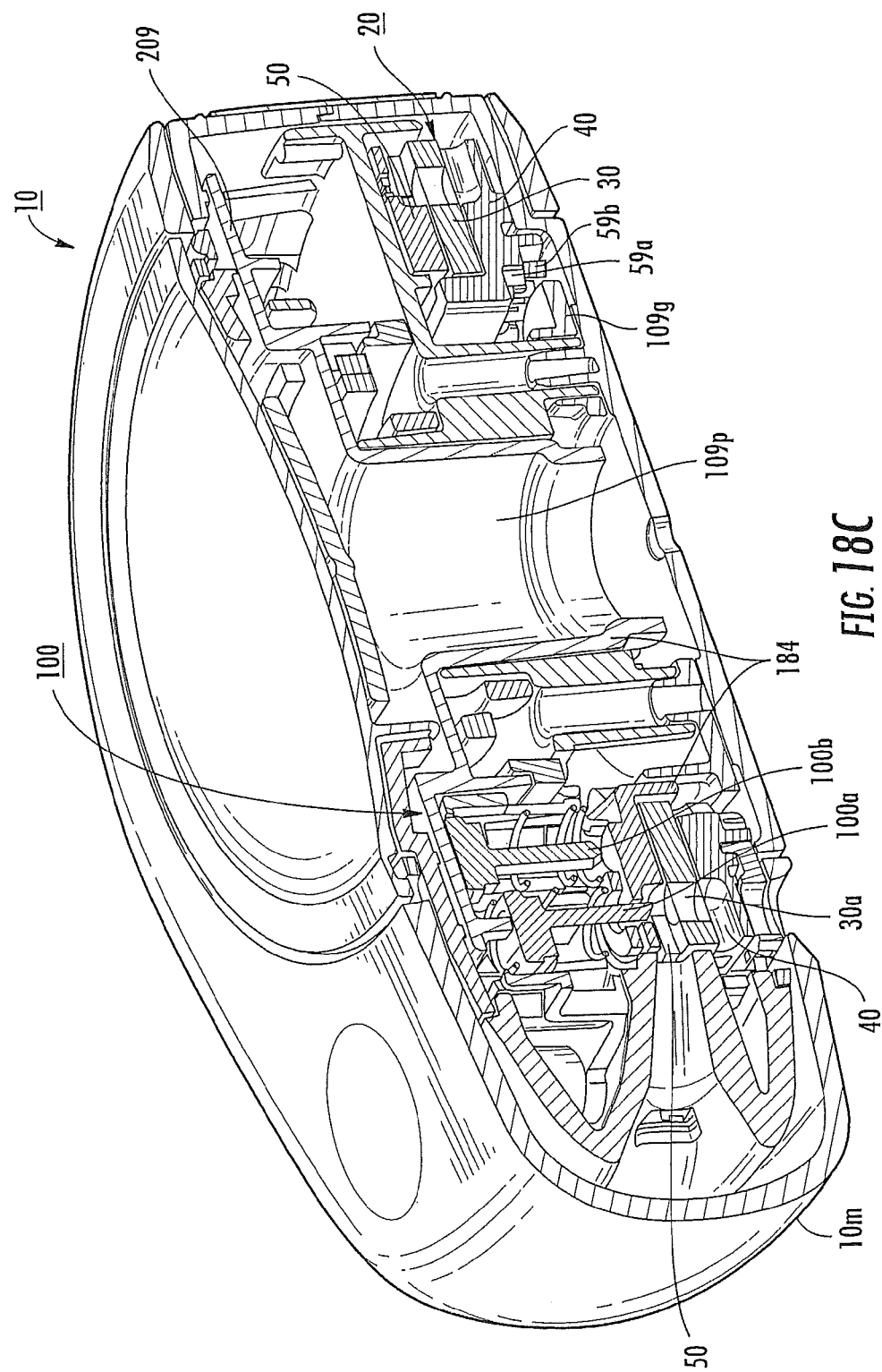
FIG. 18C is a greatly enlarged partial cutaway view of an inhaler with discrete airway channels and a short airway path according to some embodiments of the present invention.
Figure 18D:
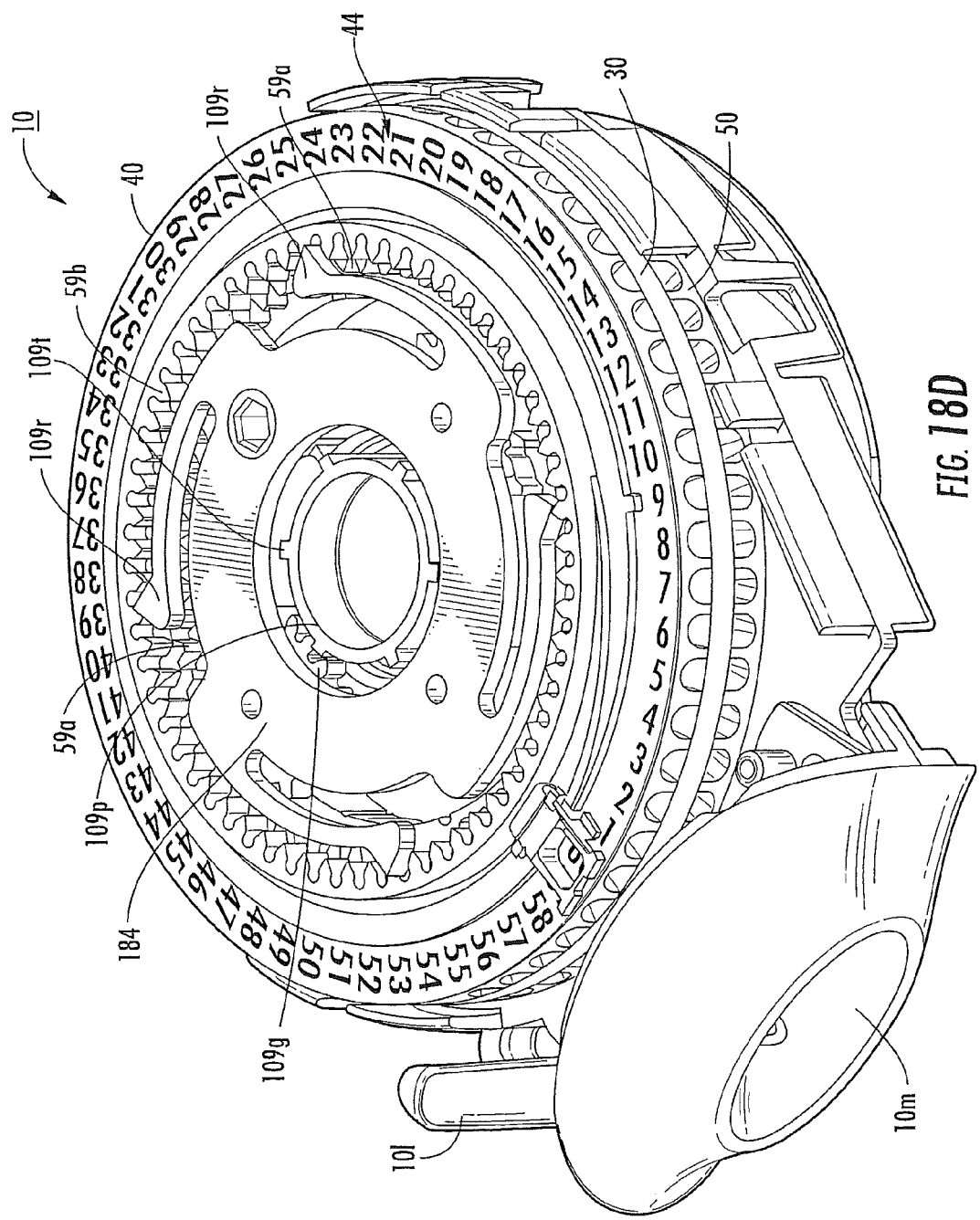
FIG. 18D is a greatly enlarged partial cutaway view of the inhaler shown in FIG. 18C illustrating an indexing mechanism according to some embodiments of the present invention.
Figure 20:
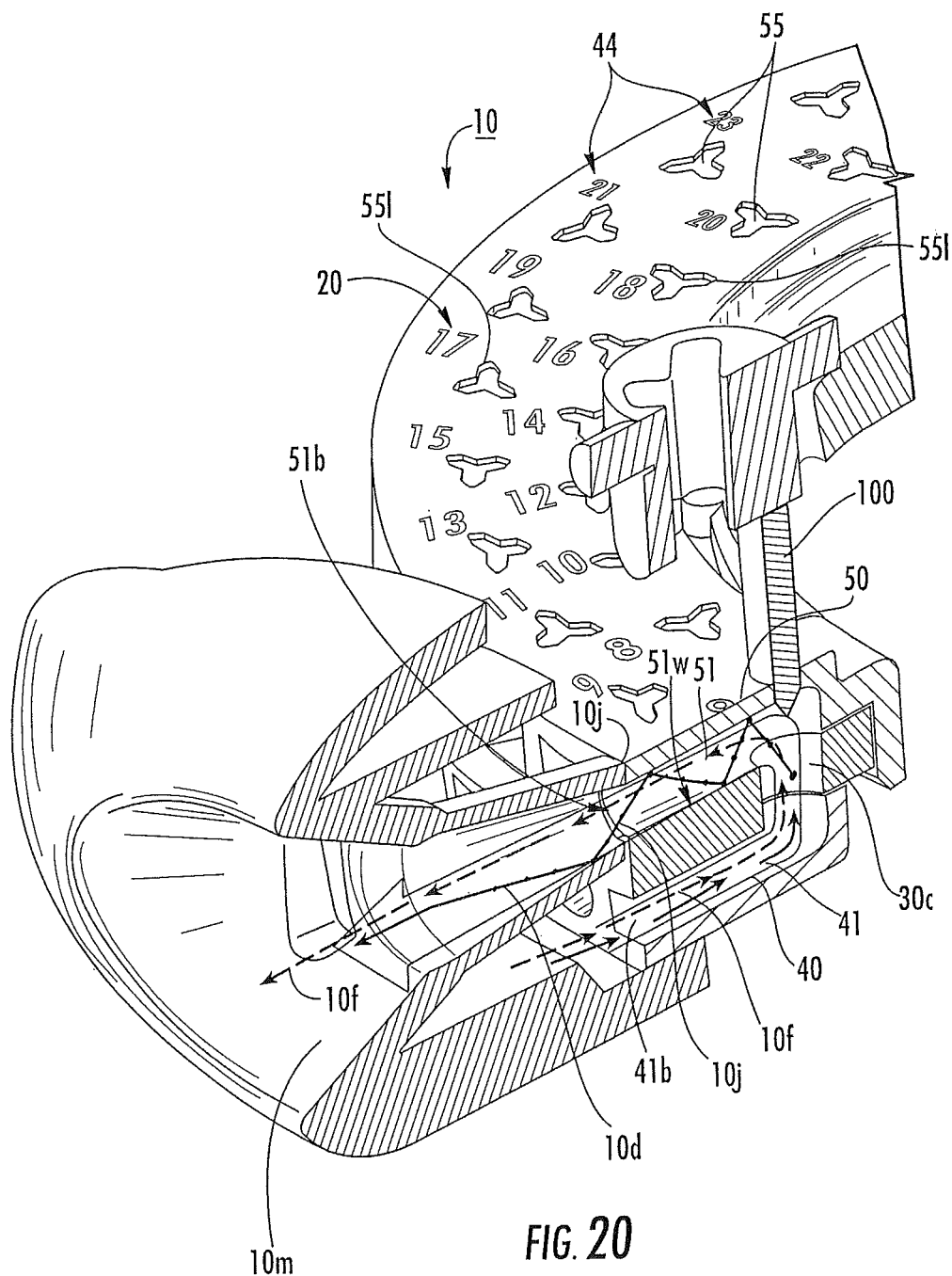
FIG. 20 is an enlarged partial section view of an inhaler having generally "U" shaped inhalation flow paths according to embodiments of the present invention.

FIGS. 4C, 18D and 20 illustrate that the disk 40 can also include dose indicia 44 so that a user can visually note what dose is being dispensed or a number of doses left in the inhaler. The dose indicia 44 can align with a dose reading aperture in the inhaler housing so that a user can visually assess the dose indicia/information that is visible to a user when a respective dose is indexed or is next to be indexed, to the dispensing position. Dose indicia 44 may also or alternatively be placed on the upper disk 50 and aligned with a dose reading aperture (FIG. 20), or on both upper and lower airway disks 50, 40, respectively.

FIG. 18D illustrates that indicia 44 may be placed along the outer perimeter edge of the lower surface of the lower disk 40, and numbered sequentially 1-60. In some embodiments, as shown in FIG. 20, the indicia 44 numbering can serially progress to alternate between rows of the dose containers 30 where the dose containers are opened in sequence in alternate rows, e.g., number 1 on the outer row, number 2 on the inner row, number 3 on the outer row (or vice versa) and so on. However, other dose numbering patterns may be used, depending on the opening sequence (and the number of doses on the disk). That is, this numbering may be appropriate where the inhaler is configured to open a dose container in one row, then open an adjacent dose container in the other row (e.g., inner to outer ring or outer to inner ring of dose containers), and repeating this sequence serially, where two rows of dose containers are used. However, other embodiments may open all the inner dose containers or all the outer dose containers, then open the dose containers in the other row or use a different alternating pattern of opening the dose containers on the inner and outer rows, and the dose numbering indicia on the disk 40 and/or 50 can be presented accordingly.

Figure 5A:
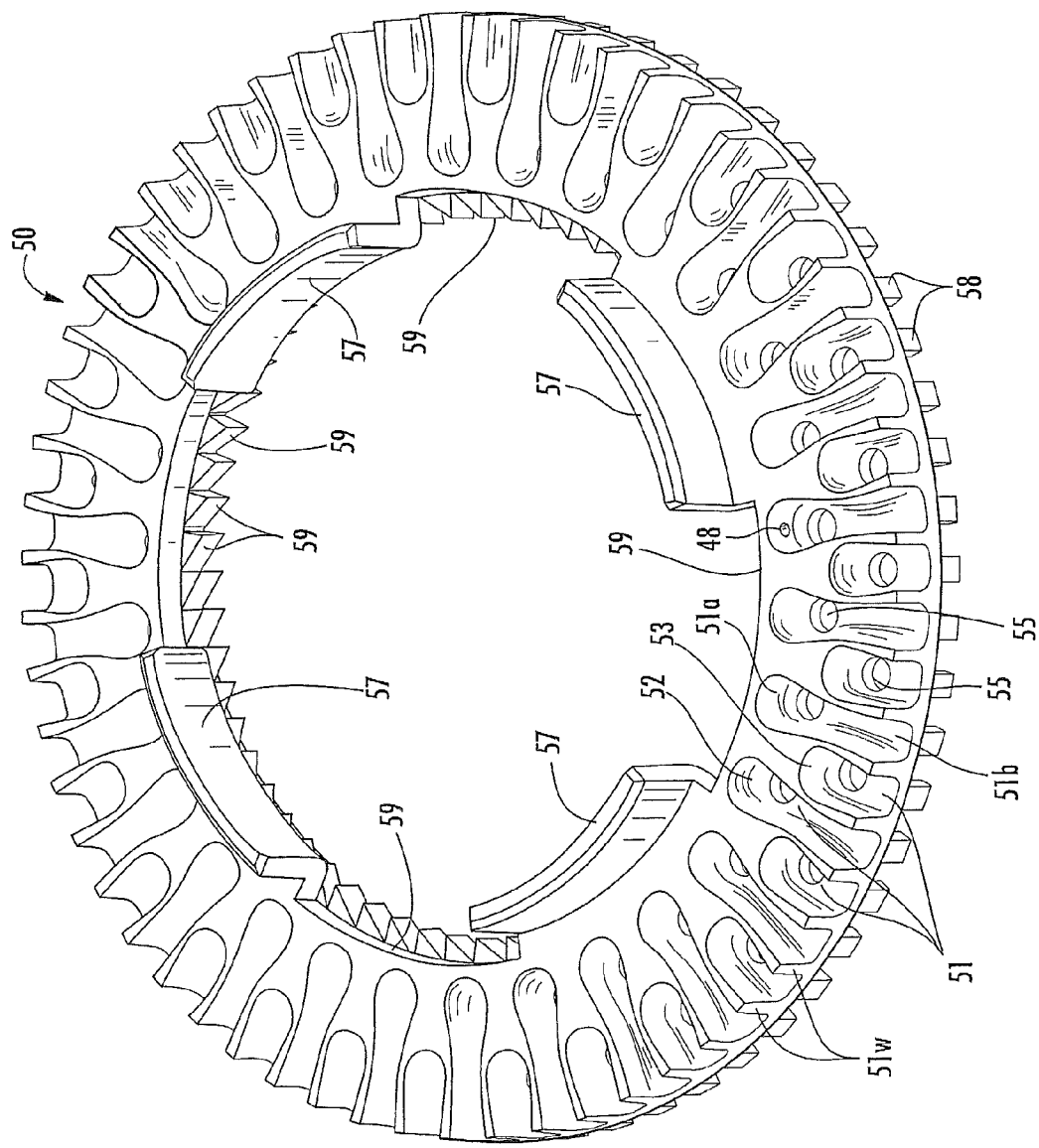
FIG. 5A is a greatly enlarged top perspective view of an upper airway disk according to some embodiments of the present invention.

FIG. 5A illustrates an example of an upper airway disk 50. In this embodiment, the upper airway disk 50 is shown inverted from its normal use position (and inverted relative to the orientation shown in FIG. 2A). As shown, the disk 50 defines a plurality of circumferentially spaced apart channels 51. For the staggered concentric dose container configuration, the disk 50 can include alternating long and short airway channels 52, 53, respectively. Each channel 51 includes opposing end portions 51a, 51b, the closed or substantially closed portion 51a is typically positioned adjacent the dose container 30c. The intake and flow can be in either direction and the open end 51b can be configured to face either the inner or outer perimeter of the disk 50 (e.g., be either positioned radially innermost or radially outermost). The other (open) end portion 51b merges into and/or is positioned adjacent the exit flow path port 10p and/or mouthpiece 10m and/or make-up air port or channel. The channels 51 include downwardly extending sidewalls 51w with adjacent pairs of the long and short channels sharing one of the sidewalls 51w. Optionally, as shown by the broken line with respect to feature 48 in FIG. 5A, one or all of the channels 51 can include a small (air) bleed hole 48 (shown with only a few channels for ease of illustration) that allows air to enter but is sized to inhibit dry powder from exiting therefrom.

As also shown in FIG. 5A, each channel 51 can include an aperture 55 that is configured to reside over (aligned with) a respective dose container 30c with the upper sealant layer 36 of the dose container 30c residing under the aperture 55. The apertures 55 allow a piercing (e.g., slicing or puncturing) mechanism to extend through the aperture and open the sealant layers 36, 37 (FIG. 3C). As shown in FIG. 5A, the upper disk 50 can also include one or more of indexing ribs 58 and/or inner perimeter gear teeth 59 or other features that can index the disk within the inhaler to rotate the disk to provide the different dose containers 30c to a dispensing position and/or position a piercing mechanism over the target dose container for dispensing to open the dose container 30c. In other embodiments, one or both of these rotating and positioning mechanisms (or different features) can be provided on the lower disk or the dose disk (not shown).

Figure 5B:
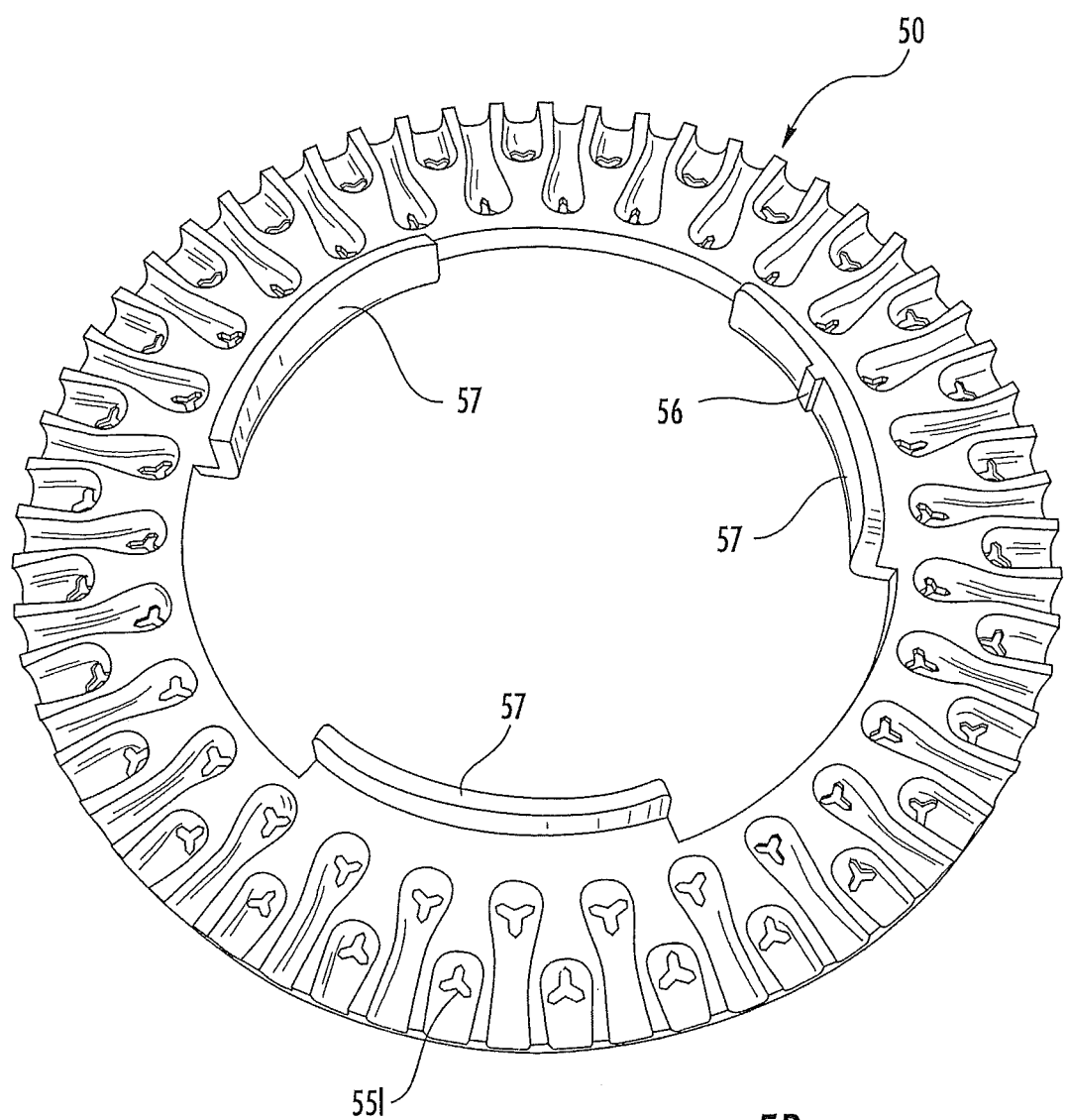
FIG. 5B is a greatly enlarged perspective view of an upper airway disk according to other embodiments of the present invention.

FIG. 5B illustrates that the disk 50 can include three tabs 57 instead of four as shown in FIG. 5A (the lower airway disk 40 can also include three tabs instead of four in this embodiment, see FIGS. 4B, 4C). One of the tabs 57 can have a vertically extending orientation rib 56, shown on an inner perimeter surface of the tab 57. The orientation rib 56 can be on the upper disk 50 and may be configured to cooperate with a piercing frame associated with the piercing mechanism fixed in the inhaler housing so that the orientation rib 56 aligns to the frame to set a correct initial position according to dose number (e.g., 1) and prevents indexing past the number of doses in the disk assembly 20. Stated differently, the orientation rib 56 cooperates with the inhaler housing or components attached thereto to set an initial position of the disk assembly 20 and may also be used to stop the disk assembly from rotating around more than once (e.g., more than 360 degrees). In other embodiments, these functions can be provided by alternate features or components such as the dose counter as described in co-assigned, U.S. application Ser. No. 12/566,724, the contents of which are hereby incorporated by reference as if recited in full herein.

The indexing of the disk assembly 20 in the inhaler 10 can be about 6 degrees for every dose (about 6 degrees for each of 60 doses to arrive at a single rotation of 360 degrees to dispense the 60 doses).

FIG. 5B also illustrates that the apertures 55 can be configured with a geometry that corresponds to the shape of the piercer 100. The apertures 55 can be configured to closely surround the piercer 100 (FIG. 20). The piercer 100 can be a fluted piercer. As shown, the aperture 55 has three lobes 551 to snugly matably receive a correspondingly shaped three lobe (fluted) piercer 111 (FIGS. 19C/19D). The fluted piercer can have other number of lobes, such as, for example four circumferentially spaced apart lobes 111' as shown in FIG. 19F and the aperture 55 can have a corresponding four lobe shape. The lobes 551 can be in a different orientation in the inner row versus the outer row, e.g., rotated 180 degrees (see also, FIG. 20).

Figure 6:
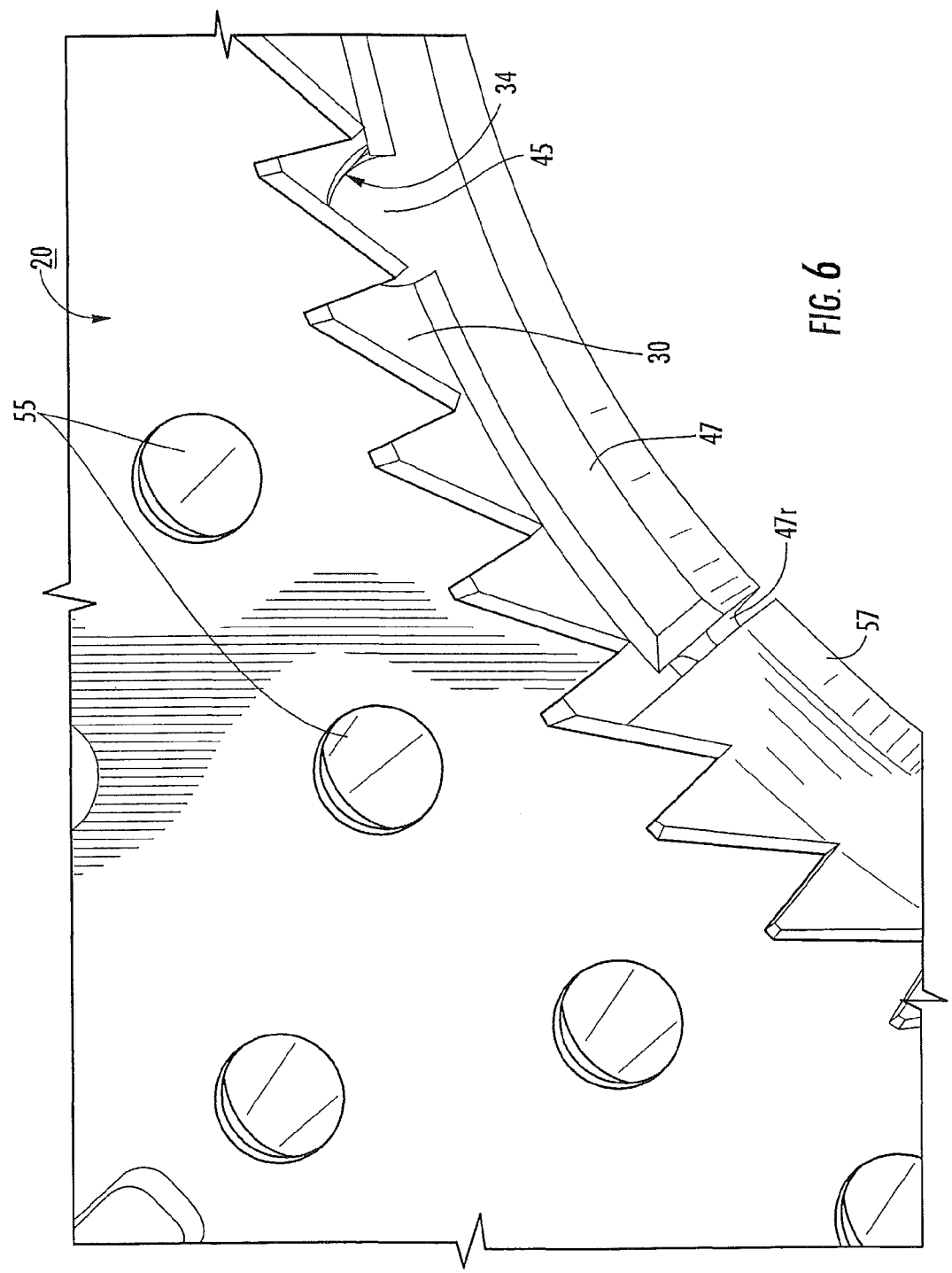
FIG. 6 is a greatly enlarged partial view of the dose container assembly shown in FIG. 2A according to embodiments of the present invention.

FIGS. 2A and 6 illustrate the dose container assembly 20 integrally attached together. FIGS. 2B, 4A, and 5A illustrate the exemplary disk components, 30, 40, 50. The tabs 57 of the disk 50 fit into spaces 49 of the disk 40 and the tabs 47 of the disk 40 fit into spaces 59 of the disk 50 with the crush ribs 47r (where used) firmly abutting the outer edges of tabs 57 to frictionally engage the components together with the dose disk 30 sandwiched therebetween with a flush fit via a relatively easy "press-fit" assembly method. The dose container disk 30 is aligned with the upper and lower airway disks via the (radially outward extending) tab 45 that engages one of the alignment notches 34 of the dose container ring 30 as discussed above. However, other alignment features or indicia may be used as well as other attachment configurations.

The upper and lower airway disks 50, 40 (where both are used) can be attached to the dose container disk 30 or the upper and lower disks 50, 40 can be attached together with the dose container disk 30 therebetween so as to reduce any gaps in the airway path defined thereby. The disk 30 can be a stop for attachment features on the airway disks 40, 50. The disk 30 with the sealants 36, 37 can have substantially planar upper and lower primary surfaces without requiring any attachment features. The lower portion of the upper airway disk 50 and the upper portion of the lower airway disk 40 can snugly reside directly against the sealant 36, 37 on the respective opposing primary surfaces of the dose container disk 30 and/or against the primary surfaces of the dose disk 30 so that the attachment features/components are only on the upper and/or lower disks 50, 40 allowing for a snug and sufficiently air-tight interface between the disks 30, 40, 50 without gaps created by tolerances in other build configurations. The press-fit attachment without use of adhesives while providing for the substantially air-tight interface can be advantageous and cost-effective. However, as noted above, other attachment configurations may be used, including, for example, ultrasonic welding, adhesive, laser weld, other friction fit and/or matable configurations, the use of seals (O-rings, gaskets and the like) between the connection regions of the walls of the airway channels facing the dose container 30c and the sealant layers 36, 37 over and/or under the dose containers 30c of the disk, including combinations thereof, and the like.

As shown in FIGS. 7A-7C, in operation, pairs of upper and lower aligned and radially extending channels 41, 51 can reside one over and one under a respective dose container 30c and are in fluid communication via the opened dose container 30c and aperture 30a. That is, as shown in FIG. 7A, a piercing mechanism 100 advances to pierce the upper and lower sealant layers 36, 37, respectively (FIGS. 2E, 3C). The piercing mechanism 100 can be configured to extend and remain in the lower airway channel or may (partially or fully) retract before the dispensing after opening the lower sealant. Also, although shown as extending down to pierce the sealant layers, the piercing mechanism 100 can be configured to extend upward from the bottom. Either way, in some embodiments, the piercing mechanism 100 can be configured to occlude part of the aperture 30a and/or aperture 55 in the upper (or lower disk).

As shown in FIG. 7B, the piercing mechanism 100 can then partially or fully retract, or stay extended in the lower (or upper) airway channel, depending on the configuration of the mechanism, but is typically configured to plug and/or cooperate with a member that can plug the aperture 55 of the upper disk 50 (or lower disk 40 if piercing from the bottom) or otherwise occlude this passage 55 so that the piercing mechanism 100 and/or cooperating member substantially blocks, occludes (and/or seals) the aperture/opening 55 (FIGS. 2A, 5A). In this way, if the inhaler is inverted, powder is prevented from spilling out of the channel 51 because of the blockage provided by the piercing mechanism 100. The airflow path 10f may be any direction from above to below the dose container 30c or vice versa. The airflow path 10f that entrains the dry powder can extend from the inner perimeter to the outer perimeter or vice versa. FIG. 7B, 20 illustrate an exemplary aiflow path 10f direction (shown by the arrow) to allow air to flow in through the open end of the bottom channel 41b on the outer perimeter of the disk assembly 20 up through the aperture 30a and out the open end 51b of the top channel 51 of the disk assembly 20 to the mouthpiece 10m. It is also noted that the exit or inlet open end portions of the channels 41b, 51b may both face the inner perimeter rather than the outer perimeter of the disc assembly 20 as shown in FIGS. 7A-7C (see, e.g., FIG. 17A).

After dispensing, the piercing mechanism 100 is fully retracted as shown in FIG. 7C and the dose container assembly 20 can be rotated to a dispensing position and/or the piercing mechanism 100 can be activated to open a different dose container 30c. In operation, the dose container assembly 20 can be radially pushed outward to seal or provide a snug exit flow path for the airway channel 41 and/or 51 against an exit flowpath member 10fm, e.g., that is or merges into the mouthpiece 10m.

FIG. 17A illustrates that a seal 129, such as an O-ring may be used to provide a sufficiently air-tight path between the airflow exit path 10l (or short path 10s and/or mouthpiece 10m) and the disk assembly 20. Other disk to exit airpath seals or closure configurations may be used, examples of which are discussed below.

In some embodiments, partial retraction of the piercer 100 can inhibit or prevent powder from falling out of the airway channel when the inhaler 10 is used in the inverted position. As shown, for example, in FIGS. 17A and 17E, to facilitate this operation, clearance between the piercer head 100h and the access aperture 55 in the upper airway disk 50 can be small and/or snugly receive the piercer head 100h. The piercer mechanism 100 can also be configured to operate with a high level of positional accuracy so that the piercer 100 aligns with and is able to cleanly enter the access aperture 55 of each dose container 30c held by the disk 30 (on each row, typically alternating between rows). In some embodiments, air leakage at the joint 10j (FIGS. 17A, 17E) between the fixed airway associated with the mouthpiece 10m and the rotating disk subassembly 20 can be reduced or eliminated to allow for consistent dose delivery and that leakage, where present, is consistent dose to dose. As discussed with respect to FIG. 17A, the use of a compliant seal (129) may allow this functionality. Also, the disk 20 can be biased toward the mouthpiece 10m as discussed above (e.g., pushed radially toward the joint 10j/mouthpiece 10m).

FIGS. 17B-17E illustrate an embodiment of the inhaler 10 that can bias the disk assembly 20 toward the mouthpiece 10m using a lever assembly 80 that can facilitate an accurate, repeatable position of the disk assembly 20 for piercing, as well as control air leakage at the mouthpiece joint 10j. With regard to air leakage, embodiments of the inhaler provide a tight connection that is temporally synchronized with the time of inhalation, while at other times, e.g., during indexing of the disk assembly 20, the inhaler can allow a looser fit which facilitates rotation of the disk assembly 20 in the inhaler 10. In this embodiment, the mouthpiece 10m resides on the outer perimeter of the disk assembly 20 with the exit ports of the disk assembly 20 also residing on the outer perimeter of the disk assembly. In other embodiments, the exit ports of the airway channels can be on the inner perimeter of the disk or otherwise configured or located.

Figure 17B:
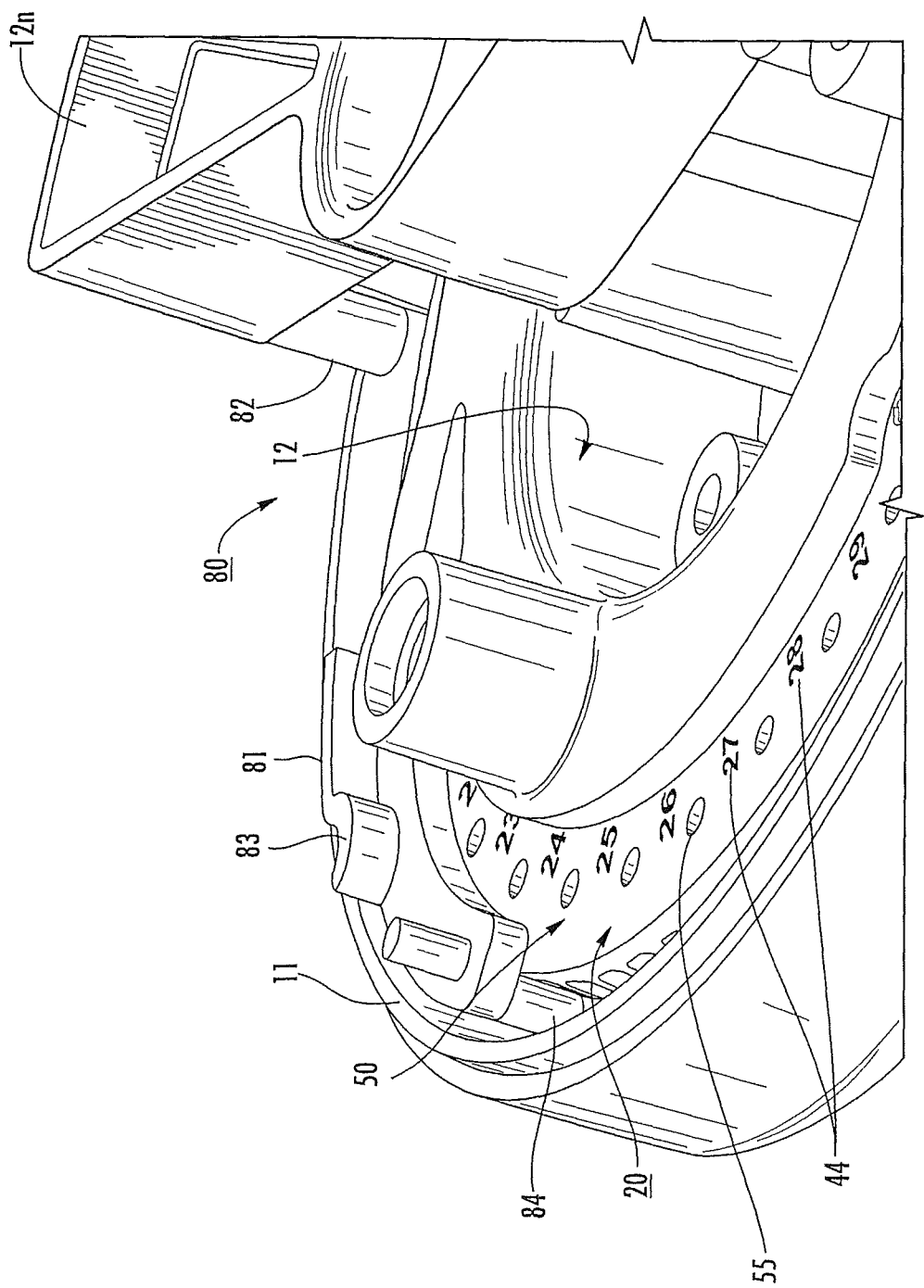

As shown in FIG. 17B, the lever assembly 80 includes a lever arm 81 that communicates with an upper surface of the upper airway disk 50 and extends down a distance to reside closely spaced to an outer perimeter of the disk assembly 20. The lever assembly 80 also includes a finger 82 that resides above the disk assembly 20 and extends down toward the disk assembly 20. In the embodiment shown, the lever assembly 80 also includes a loading post 84 that resides proximate an outer perimeter of the disk assembly 20. The lever arm 81 includes a recess 83 that is configured to receive the finger 82. As the finger 82 resides in the recess 83, the post 84 post pushes the disk 20 radially inward to causes a tight joint 10j at the time of inhalation (FIG. 17E).

The recess 83 can have an open perimeter shape and the finger 82 can slidably enter and exit therefrom. The lever arm 81 can define a ramp (inclined in the direction toward the recess 83) that slidably engages the finger 82 and directs the finger 82 to move toward the recess 83.

The lever assembly finger 82 is attached to lever 12n (also labeled as 10l in FIG. 1B) and rotates with respect to the frame 12 in the inhaler housing, typically upon user actuation of the lever 12n. When the lever 12n is returned from "actuated" (dosing) position, the finger 82 is pulled out of the recess 83 so that the disk assembly 20 is free to rotate to index to a next dispensing position.

Typically during inhalation, the loading post 84 resides radially opposite (substantially diametrically opposed to) the mouthpiece 10m. The lever arm 81 and post 84 do not rotate. This component is affixed to a frame 12 that is attached to the inhaler housing. The finger 82 rotates with respect to the frame 12 (and the lever arm 81).

Figure 17C:
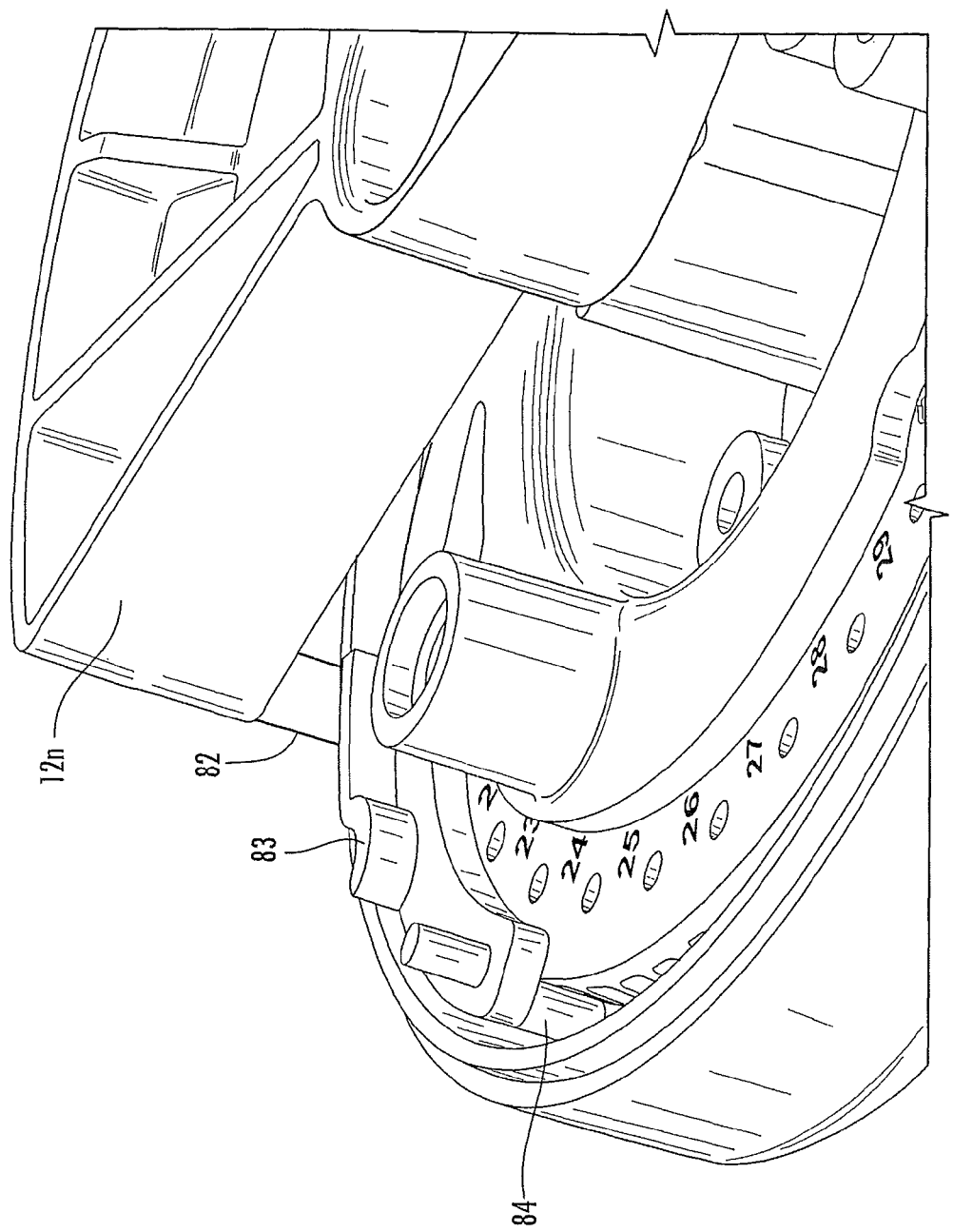

As shown in FIG. 17B, the finger 82 does not contact the lever arm 81 during this portion of the stroke cycle of the lever assembly 80 to allow for free rotation during indexing. FIG. 17C illustrates the finger 82 moving toward the recess 83. FIG. 17D illustrates the finger 82 in the recess 83 to bias the disk assembly 20 toward the exit flow path member 10fm. At the moment of inhalation, the finger 82 is advanced to its fullest extent of travel. Indexing (rotation) of the disk assembly 20 occurs while the finger 82 is elsewhere in its travel path. Therefore, as shown by the arrows in FIG. 17D, the lever assembly 80 can bias the disk assembly 20 while the finger 82 is at the far extent of travel to seal the joint 10j at the proper time (inhalation), while allowing free movement during indexing (typically also unbiased the rest of the time).

It is recognized that, during manufacturing, there may be a tolerance-induced mismatch between the diameters of the dose disk 30 and the upper airway disk 50 of the disk assembly 20. As shown in FIG. 17E, inner or outer sidewall surfaces (shown as outer sidewall surfaces) of both of these disks, 30, 50 contact the mouthpiece 10m when the disk assembly 20 is biased against it. Thus, as shown in FIG. 17E a small relief 10r can be cut or otherwise formed into the proximate or abutting surface of the an exit flowpath member 10fm (which may be the mouthpiece 10m) at a location that coincides with the dose disk 30 to assure that the upper airway disk 50, which has the greater amount of contact surface, is always the part to contact the mouthpiece or exit flowpath member 10fm in communication with the mouthpiece 10m.

Figure 17F:
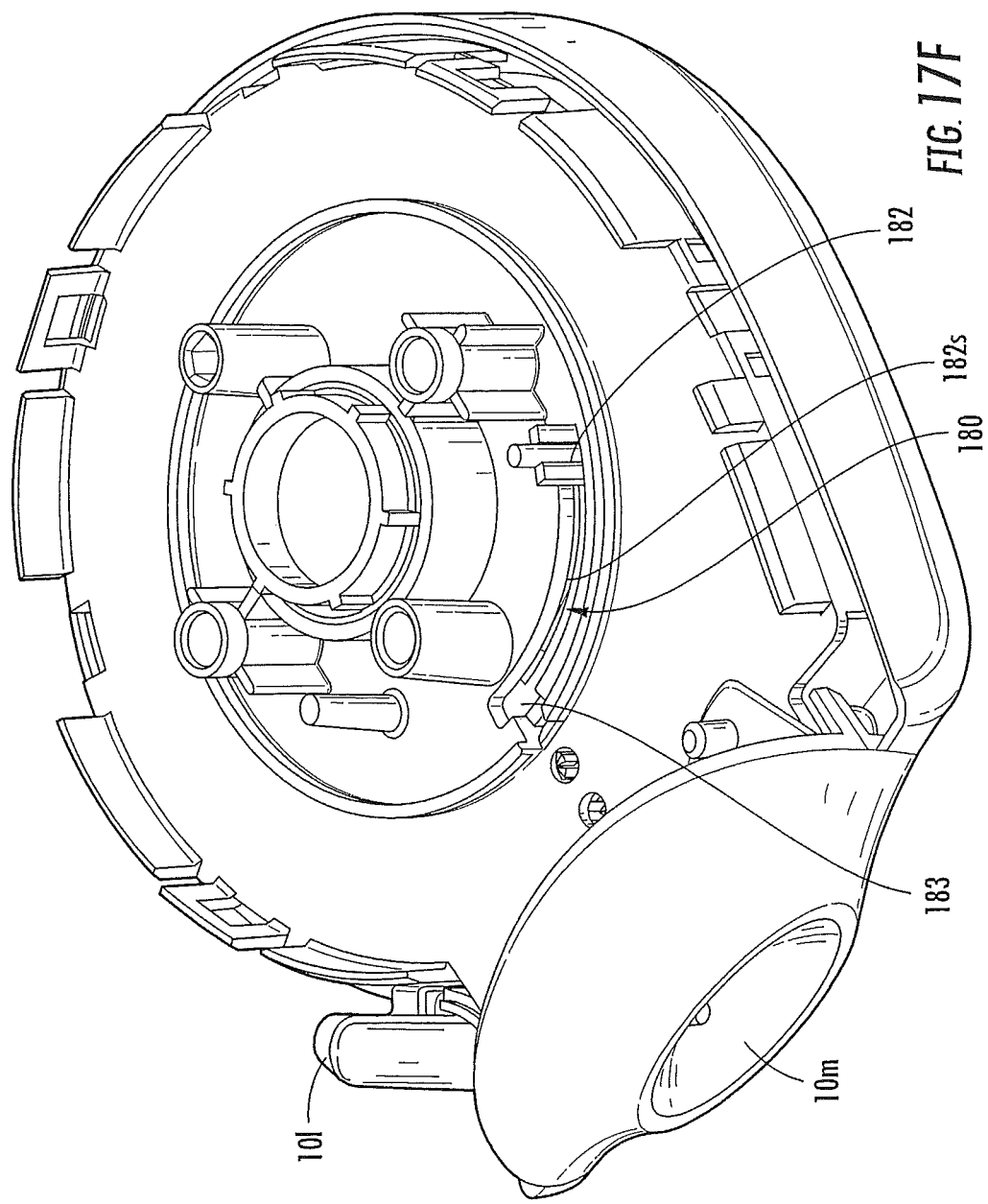
FIG. 17F is a perspective partial cutaway view of an inhaler with an alternate biasing mechanism (shown inverted from normal orientation) according to embodiments of the present invention.
Figure 17G:
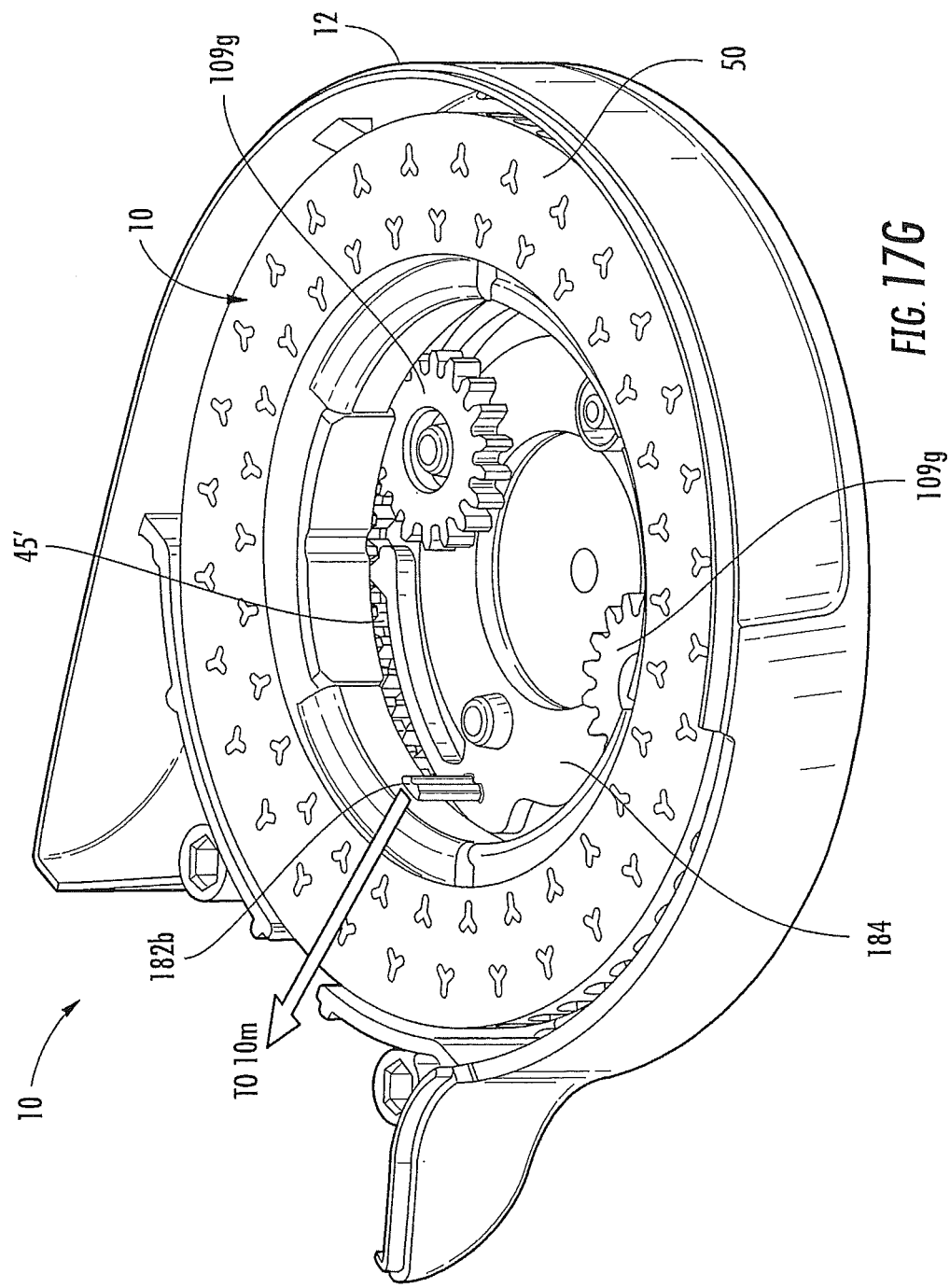
FIG. 17G is an additional perspective view of the biasing mechanism shown in FIG. 17F.

FIGS. 17F and 17G illustrate an alternate embodiment of a biasing mechanism 180 that can bias the disk assembly 20 toward the mouthpiece 10m during inhalation then releasing or disengaging to allow rotation of the disk assembly 20 for indexing. As discussed above, in some embodiments, the inhaler 10 can be configured to rotate the disk assembly 20 a defined angular rotation, such as about 6 degrees, to serially dispense or access dose containers alternately on inner and outer rows. This biasing mechanism 180 can be configured to operate with the lever 10l similar to that discussed above with respect to the lever assembly 80 but may also be activated using other components or features.

As shown in FIG. 17F, the biasing mechanism 180 can include a post 182 that resides proximate an inner perimeter of the dose container disk assembly 20. The post 182 can reside in a circumferentially extending slot 182s having an end portion that merges into a slot portion 183 that extends radially outward toward the inner perimeter of the dose disk assembly 20. During and/or just prior to release of the medicament to a user for inhalation (e.g., "dosing"), the post 182 travels in slot 182s until it reaches slot portion 183 whereby the post moves radially and pushes (typically indirectly) against the inner perimeter of the disk assembly 20 to bias the disk assembly 20 toward the mouthpiece 10m (as shown by the arrow). The inhaler is shown upside down from normal orientation in FIG. 17F.

FIG. 17G illustrates that the post 182 can communicate with a stationary post 182b on an indexing plate or frame 184. In the embodiment shown, the biasing post 182 is configured to contact and push against post 182b causing post 182b to flex radially outward against the dose container assembly 20. The two posts 182, 182b can be configured to project toward each other, one upwardly and one downwardly, with the post 182b typically residing closer to an inner perimeter of the dose disk assembly 20.

The post 182 is typically attached to or in communication with the lever 10l which is accessible by a user. However, the post 182 can be in communication with other mechanisms that cause the post 182 to move in the slot 182s and bias the disk assembly 20 toward the mouthpiece 10m.

Figure 18E:
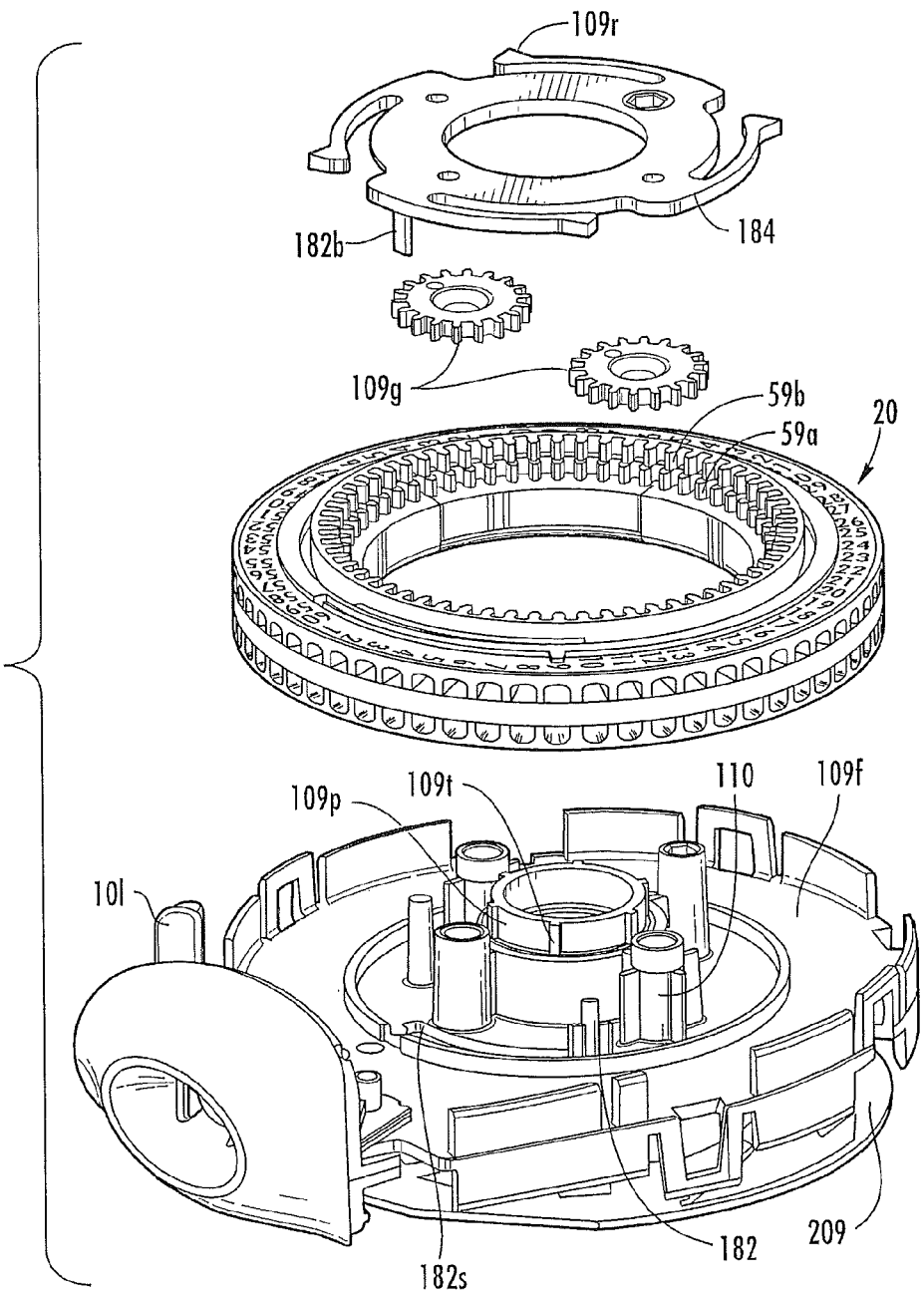
FIG. 18E is an exploded side perspective view of components of the indexing mechanism shown in FIGS. 18C and 18D.
Figure 18F:
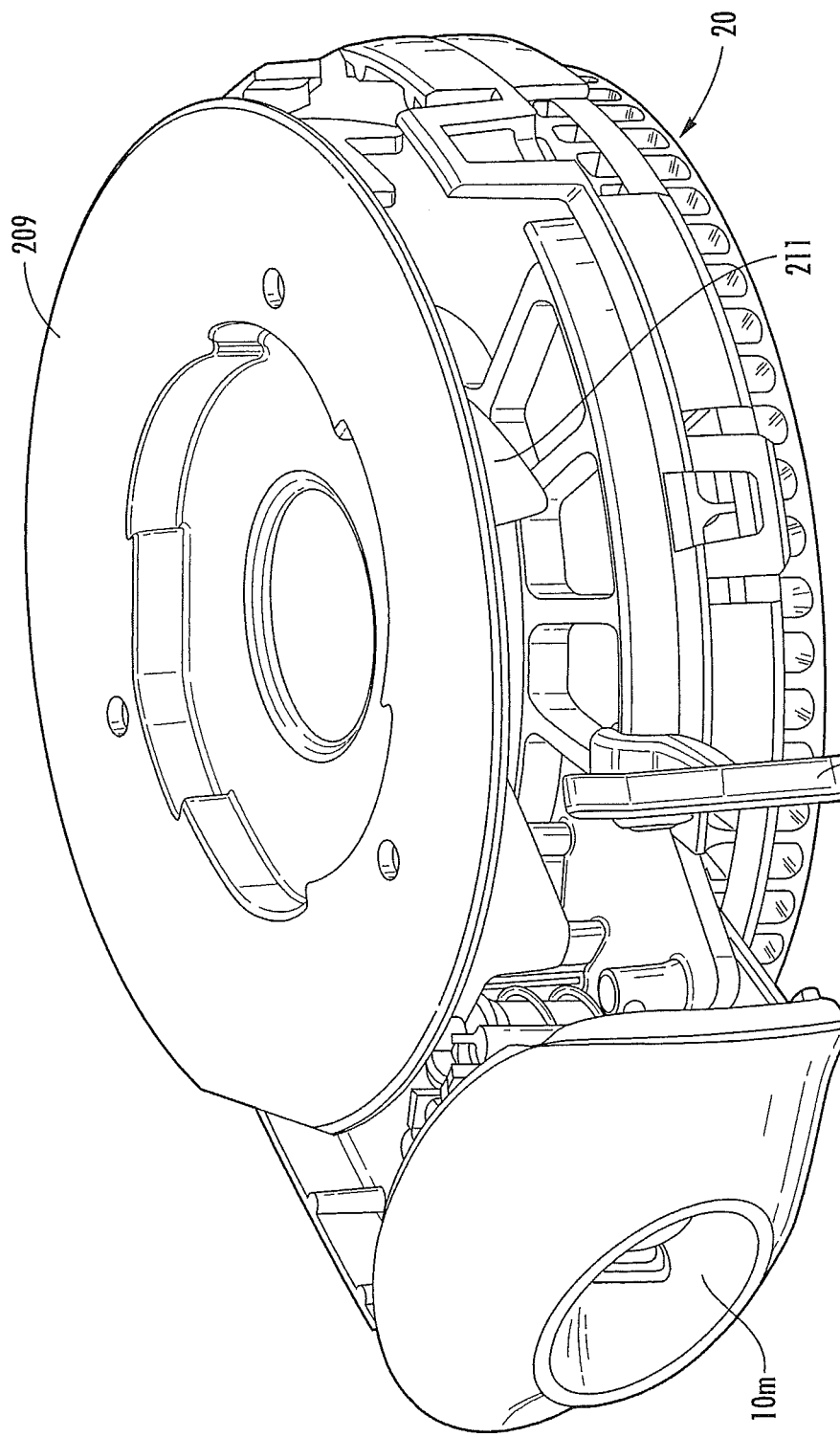
FIG. 18F is an enlarged side perspective view of some assembled components of the inhaler devices shown in FIG. 18E.

As shown in FIG. 17G, the indexing plate 184 can reside under gears 109g that are associated with the indexer 109. The rotatable gears 109g can be held on mounts 110 on a frame member 109f as shown in FIG. 18E. Generally stated, the gears 109g communicate with teeth 109t on indexing post 109p that can be part of a ramp disk 209 (FIG. 18F) and gear teeth 59a on the disk assembly 20 (e.g., as shown, on the lower disk 40). Turning the indexing post 109p turns gears 109g which, in turn, indexes the disk assembly 20. The other gear teeth 59b (residing closer to the bottom of the inhaler housing) can communicate with indexing control arms 109r as shown in FIG. 18D which can help more precisely turn the dose container assembly a desired rotational amount. Note that FIGS. 18D and 18E illustrate the inhaler in an inverted orientation from that of normal use. FIG. 18F shows the inhaler in a "normal" use orientation with the dose disk assembly 20 below the piercers 100a, 100b as also shown, for example, in FIG. 18C. The piercer(s) 100a/100b can be in communication with the ramp disk 209 with fin-like ramps 211 as shown in FIG. 18F. In the embodiment shown, the ramp disk cooperates with the piercer to push the piercer into the respective dose containers 30c. The post 182 is typically attached to the lever 101 such as shown in FIGS. 17F, 18E and 18F which is accessible by a user. However, the post 182 can be in communication with other mechanisms that cause the post to move in the slot 182s and bias the disk assembly 20 toward the mouthpiece 10m.

The indexing mechanism 109 shown in FIGS. 17F and 17G is discussed further below with respect to FIGS. 18C-18F. However, other indexing configurations can be used.

Figure 19A:
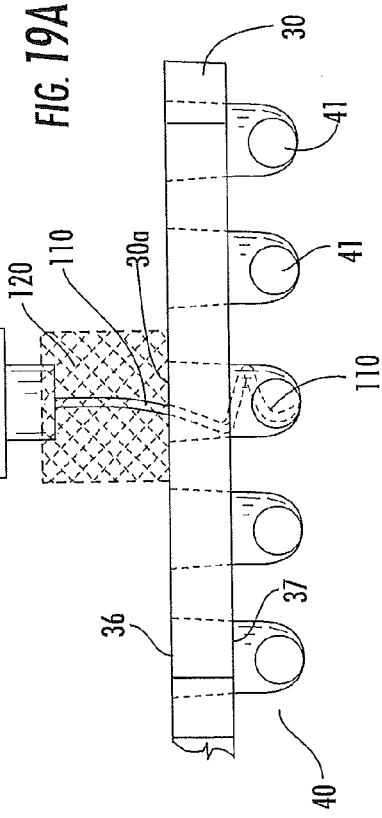
FIG. 19A is an enlarged partial section view of an alternate piercing mechanism for the dose containers according to some embodiments of the present invention.
Figure 19C:
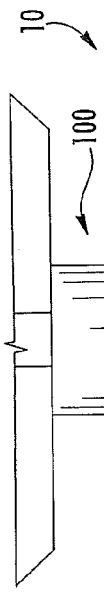
FIG. 19C is a partial front schematic view of a piercing mechanism with a fluted piercer according to some embodiments of the present invention.
Figure 19B:
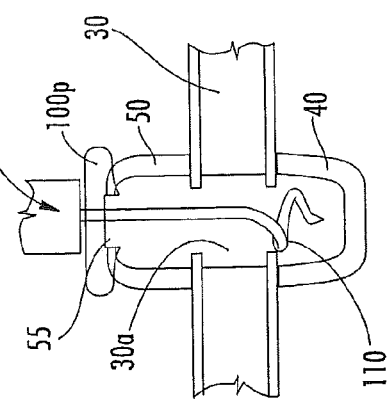
FIG. 19B is an enlarged partial section view of a piercing mechanism similar to that shown in FIG. 19A according to some embodiments of the present invention.

FIG. 19A illustrates one embodiment of a piercing mechanism 100 with a corkscrew piercer 110. In operation the corkscrew moves up and down vertically straight, typically without rotation, to create a desired opening shape (e.g., circular) through the sealant layers 36, 37. In other embodiments, the corkscrew may rotate during extension and/or dispensing. In the embodiment shown, the corkscrew piercer 110 can remain in the lower channel 41 while the dry powder is dispensed in the airflow path and the blockage of the aperture 30a can be provided by a resilient member 120 that is mounted on the corkscrew 110 and moves up and down therewith. The piercing mechanism 100 can have a two stage operation, fully up (for indexing) and fully down. The most forward portion of the corkscrew can have a point with a configuration that creates a desired cutting configuration into the sealant (e.g., foil). In some embodiments, the corkscrew piercer 110 can cut a shape with a tab into the sealant 36, 37, then fold the tab down to release the dry powder. Positioning the corkscrew piercer 110 in the channel 41 during dispensing may provide improved aerodynamics or shear or impaction flow turbulence for the dry powder. The resilient member 120 can comprise a foam block or other resilient member 120 (such as a hard or rigid member biased by a spring) that can be used to seal or plug the aperture 30a. FIG. 19B illustrates a similar corkscrew piercer 110 that is used with a disk assembly 20 having both upper and lower airway disks 50, 40. A resilient and/or flexible member 100p such as a polymeric and/or elastomeric or foam plug can be used to occlude or seal the disk aperture 55.

Figure 19D:
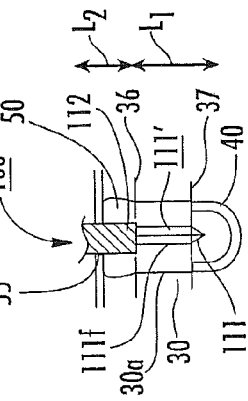
FIG. 19D is an end view of the device shown in FIG. 19C.
Figure 19E:
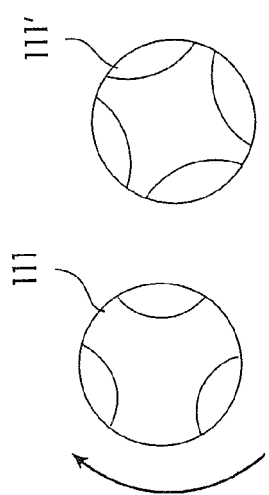
FIG. 19E is a partial front schematic view of another fluted piercer configuration according to some embodiments of the present invention.
Figure 19F:
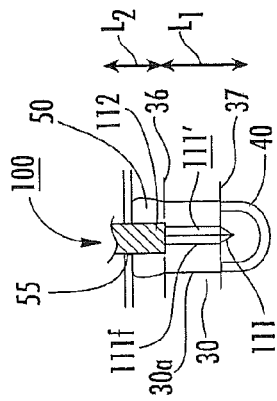
FIG. 19F is an end view of an exemplary four lobe fluted piercer according to some embodiments of the present invention.

FIGS. 19C and 19D illustrate a piercing mechanism 100 with a fluted solid piercer 111. The flute may have a straight flute configuration or the flute can have a twist or partial twist along it length, e.g., for a twist configuration, the maxima and minima of the lobes can change axially along the length of the flute. The flute can have a cross section with a plurality of lobes, typically three or four lobes, shown as three lobes in FIG. 19C. The fluted configuration may extend only a partial forward length and merge into a constant diameter segment that resides in and helps occlude or seal the aperture 55 as shown in FIG. 19E. In other embodiments, the solid or fluted piercer configuration can merge into a cap or plug 100p that resides over and/or in the aperture 55 (see, e.g., FIG. 19C). In some embodiments, the twisted flute 111 can remain in the dose container aperture 30 and/or lower disk 40 during dispensing which may facilitate turbulence and/or compaction in the airway.

FIG. 19D illustrates that the fluted piercer 111 can rotate as it pierces the foil or other sealant material to form a round hole or may be extended straight without rotation. In other embodiments, the fluted piercer 111 can be extended or advanced without rotation to pierce the sealant layer(s) 36, 37. FIG. 19E illustrates that the fluted piercer 111' can include a fluted forward portion 111f with a length "$L_1$" that merges into a solid portion 112 that can have a substantially circular cross-section with a length "$L_2$". $L_1$ is typically longer than $L_2$. $L_1$ can have a length sufficient to allow the forward fluted portion 111f to reside in the dose container aperture 30a (typically just below the lower sealant line or in-line with or slightly above or below the lower surface of the disk 30) and in or through the lower sealant 37 at the same time, with the solid portion engaging the airway disk aperture 55.

Figure 19G:
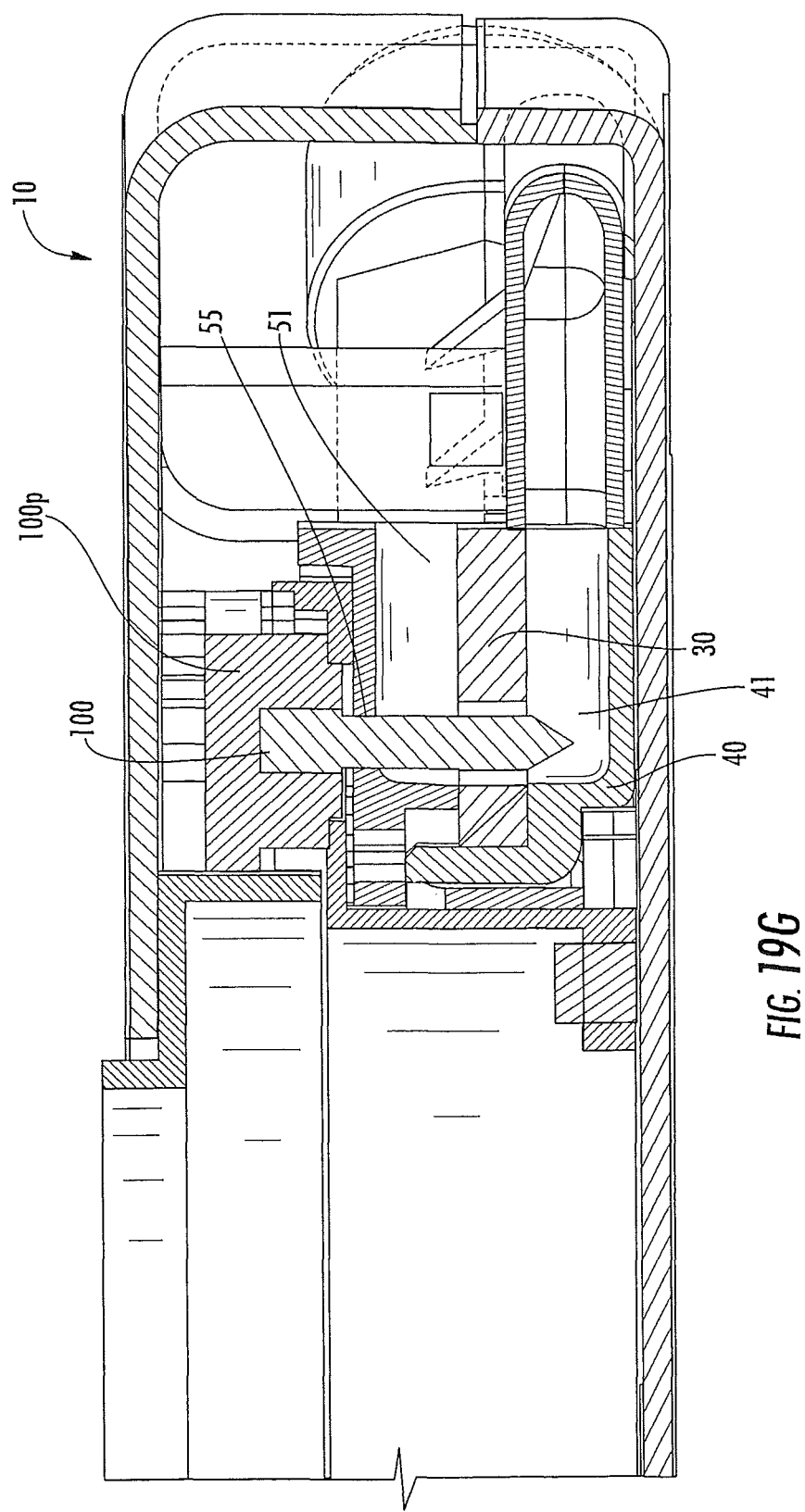
FIG. 19G is a partial cutaway schematic illustration of an inhaler with a piercing configuration according to some embodiments of the present invention.

FIG. 19G illustrates a piercing mechanism 100 that can include a plug 100p (similar to that shown in FIG. 19B for the corkscrew configuration) that can occlude the passage 55. The plug 100p can be used with any piercer, including the corkscrew 110 (FIG. 19A) or the solid fluted piercer 111 (FIG. 19B) or other piercer configuration. The piercing head can remain in the lower channel 41 during dispensing as shown in FIG. 19E, or the piercer may retract partially through a passage in the plug (not shown) while leaving the plug 100p in position against and/or over the aperture or passage 55.

In some embodiments, the fluted piercer 111 can be configured with lobes that twist along its length (FIG. 19D). For example, the fluted piercer 111 can have about 60 degrees of twist along its length such that the lobes of the fluted piercer turn about its circumference. During a straight piercing stroke (straight into and through the sealant), the twisted fluted piercer 111 can make a fully round hole in the sealant 36 and/or 37.

FIG. 20 illustrates substantially U-shaped airpaths that may be created by the disk assembly 20. The "U" shape is created by the upper disk channel 51 and the lower disk channel 41 defining the long sides of the "U" which extend in a radial direction across the disk body. As shown, in this embodiment, the outer perimeter of the disk assembly 20 holds both the outlet and an inlet for the airflow path 10f. The "U" shaped flow path (or, in some embodiment, a" partial "U" where only a one of the airflow disks 40, 50 is used) can function as a powder deagglomerator. The particles impact the opposing wall of the airway disk channel 51 as they exit the dose container 30c with sufficient force to deagglomerate the drug powder.

FIG. 20 also illustrates an example of dry powder particle trajectories 10d entrained in air flow associated with the inspiratory airflow path 10f. After the dry powder exits the dose container 30c in the airflow path 101, the air flow and smaller powder particles (10f) in the air are able to make the about 90 degree turn while heavier dry powder particles (10d) bounce off the inner wall 51w of the upper airway disk channel 51 with increasingly shallow angles eventually going more or less straight out of the mouthpiece 10m. The impact of the heavier dry powder against the walls 51w help deagglomerate the dry powder. Referring again to FIG. 5A, in the dual row dose container 30 embodiment, the channels 51 vary in length depending on if the dose container 30 is on the inner or outer row.

In some particular embodiments, the airway channels 41, 51 can include alternating short and long channels (see, e.g., FIG. 5A). The length of the long channel (the channels with the dose container on the inner perimeter where the outer perimeter is the exit location and vice versa if the inner perimeter is the exit location) can between about 5 mm to about 15 mm, typically about 10 mm, the length of the short channel can be between about 3-10 mm, typically about 5 mm, e.g., about 40-70% the length of the long channel. The depth (vertical height) of each channel 41, 51 can be the same or can, in some embodiments vary. Exemplary depths of the channels 41, 51 are between about 1 mm to about 3 mm, typically about 2 mm, but other depths can be used.

The inhaler 10 can include a user-accessible actuator such as a lever, knob, switch, slider, crank, pushbutton or other mechanical and/or electromechanical device that can index the dose ring or disk 30 to rotate the assembly 20 to place one or more dose containers 30c (FIG. 2B) in a dispensing position in an inhalation chamber in fluid communication with the inhalation port 10p (FIG. 1B) and/or cause a piercing mechanism 100 (FIGS. 7A-7C) to open a dose container 30c in the front row, then the back row (or vice versa) to release medicament to an inhalation air flow path for inhalation by a user (as will be discussed further below). To release the powder for inhalation, the sealed dose container 30c is opened and connected to an airway 41 and/or 51 which is in turn connected to an exit flowpath member 10fm which can be the inhaler mouthpiece 10m (see, e.g., FIGS. 7A-7C, 17A, 17E, 18A) or can merge into the inhaler mouthpiece 10m. After the drug falls into the channel 41 or 51 (depending on which orientation the inhaler is in), this is a "used" channel and the drug therein is either delivered (if the user inhales properly and timely) or isolated (if the user does not inhale and closes the mouthpiece or otherwise causes the indexing of the disk assembly 20), and the "used" channel is indexed with the opened dose container 30c so that it cannot be used again or so that it is used again for only the other dose container in the shared channel (as discussed with respect to FIG. 2C). Any powder remaining in the opened dose container is separated from the airway when the next dose container is indexed into position.

In some embodiments, the portion of the airway provided by the airway channel 41 or 51 adjacent to each dose container 30c is unique to that individual dose container 30c. In this way, any spillage of powder into the airway will only be available to the mouthpiece and user as long as that dose container is indexed into connection with the primary (mouthpiece) airway. Indexing to the next dose container will also index the adjacent airway section out of connection with the active inhalation airway path, taking any spilled and/or accumulated powder with it.

Figure 8A:
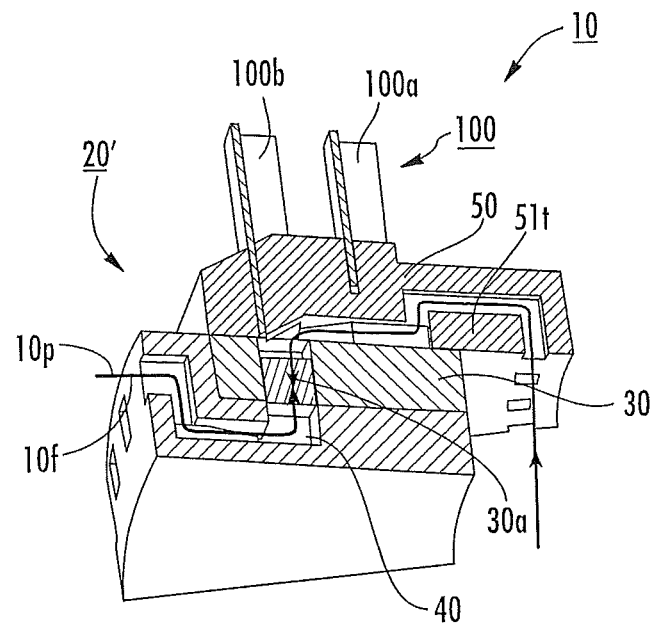
FIG. 8A is a bottom perspective partial cutaway view of an inhaler with a dose container assembly configured so that the outer ring of dose containers are aligned with airway channels in disks that have "sink traps" to inhibit spillage according to some embodiments of the present invention.
Figure 8B:
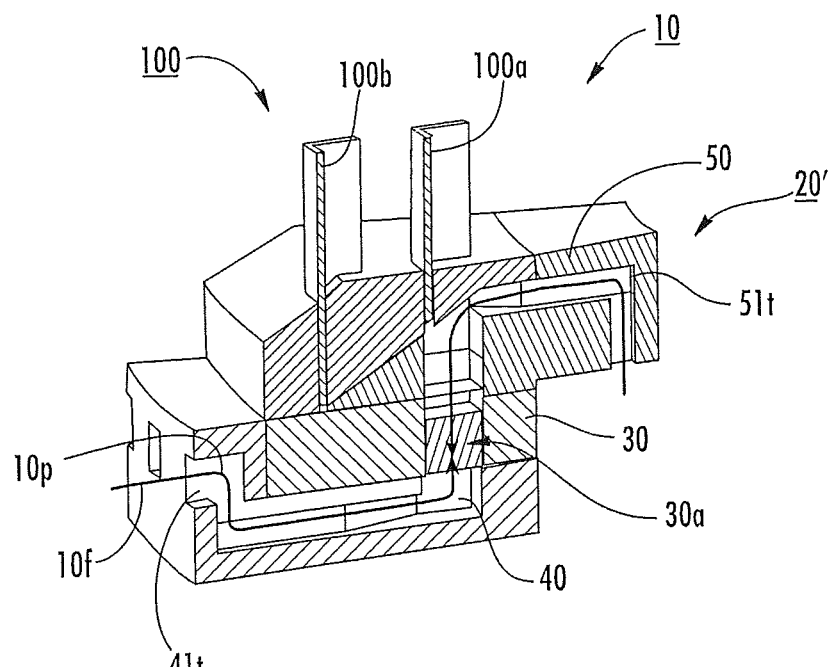
FIG. 8B is a side perspective view of the device shown in FIG. 8A illustrating the inner row of dose containers are aligned with airway channels in disks that define "sink traps" to inhibit spillage according to some embodiments of the present invention.
Figure 9A:
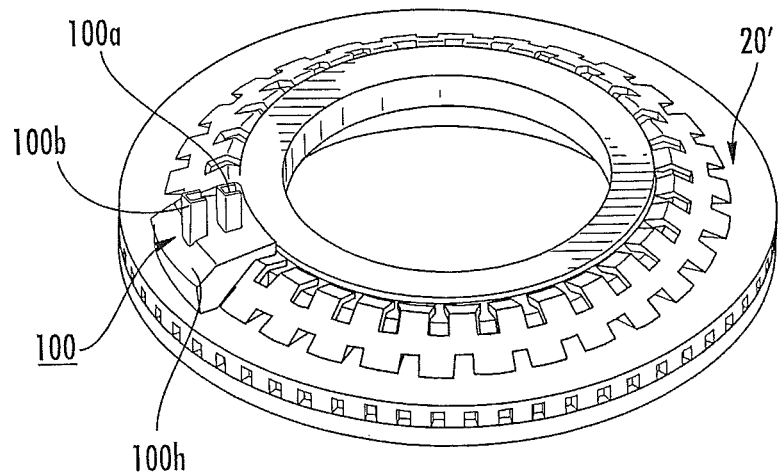
FIG. 9A is a top perspective view of a dose container assembly and piercing mechanism according to some embodiments of the present invention.
Figure 9B:
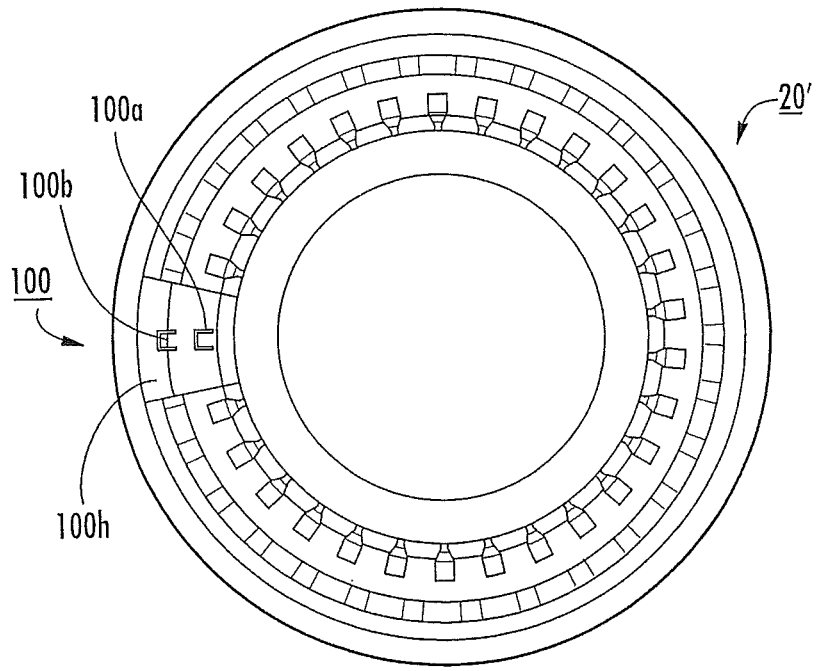
FIG. 9B is a top view of the device shown in FIG. 9A.
Figure 9C:
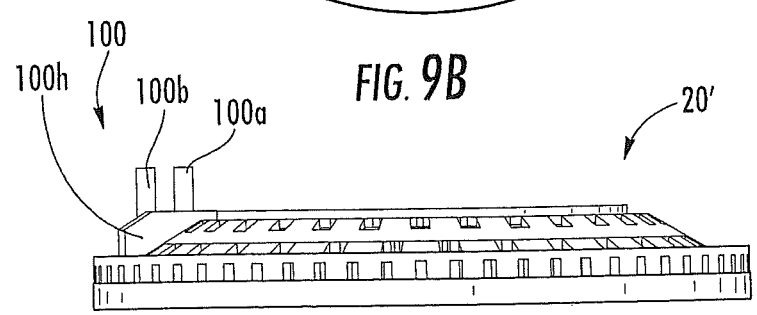
FIG. 9C is a side view of the device shown in FIG. 9A.
Figure 13:
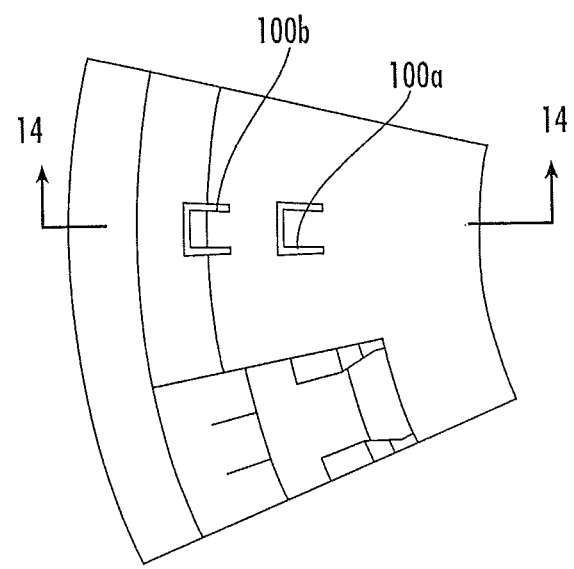
FIG. 13 is a top assembled view of the portion of the device shown in FIG. 10.

FIGS. 8A and 8B illustrate another embodiment of an inhaler 10. In this embodiment, the upper airway channel 51 can be configured as a "sink trap" 51t path that has a portion of the airflow path that rises and then turns down or vice versa. That is, as shown, the path 51t can rise above the aperture 30a, then turn to extend downwardly for a distance to provide additional spill resistance of the dry powder from the airway/inhaler. Similarly, the lower airway channel 41 can be configured to rise upward a distance downstream of the dose container aperture 30a to form a "sink trap" 41t path. In some embodiments, only one of the airway disks (e.g., the upper or the lower 50, 40) have a sink trap path while in others, both disks 40, 50 have airway configurations with sink traps 41t, 51t as shown. The dose container assembly 20 has an aligned channel pair 41, 51 that are in fluid communication once the respective dose container is opened 30c that reside under and over the respective dose container 30c and have the sink trap configurations 41t, 51t to that cooperate to form a curvilinear airflow path (e.g., a generally "S" shape, with the "S" layed on its side). The airflow path 10f can extend either from the outer perimeter toward the inner perimeter or from the inner perimeter toward the outer perimeter.

As also shown in FIGS. 8A and 8B, in this embodiment, the piercing mechanism 100 can include two piercing members 100a, 100b, one dedicated to opening the first row of dose containers 30c and another for the second row of dose containers 30c.

FIGS. 9A-9C and 10-14 illustrate an exemplary inhaler configuration with upper and lower airways forming a sink trap 51t, 41t airflow path according to embodiments of the present invention. As shown, the piercing mechanism 100 can include the two piercing members 100a, 100b mounted on a housing that slides over the dose container assembly 20'. The dose container assembly 20' can rotate under the piercing mechanism 100 as a respective dose container(s) 30c is indexed to a dispensing position. Similarly, the dose container assembly 20' can rotate above the piercing mechanism if the piercing mechanism is below the dose container assembly 20, 20'.

Figure 14:
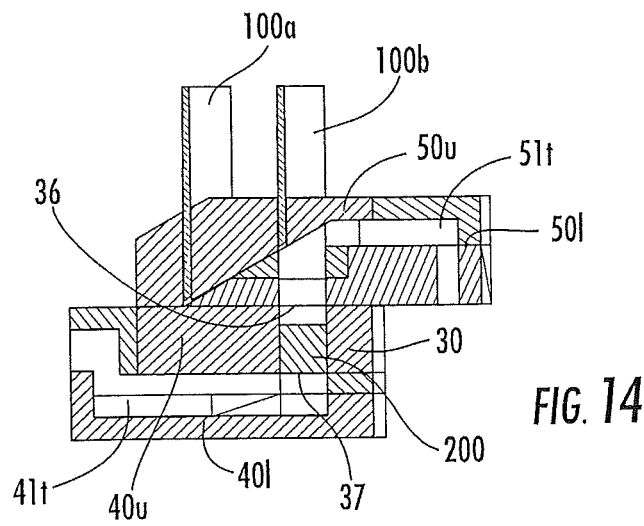
FIG. 14 is a side section view taken along lines 14-14 of FIG. 13, illustrating an inner ring actuation according to embodiments of the present invention.

FIGS. 10, 12 and 14 illustrate that the lower airway disk 40 can include two components, an upper member 40u and a lower member 40l that attach to define the curvilinear sink trap paths 41t. Similarly, the upper airway disk 50 can include two components, an upper member 50u and a lower member 50l that attach to define the curvilinear sink trap paths 51t. In particular embodiments, the dry powder can be provided as a pre-measured amount of dry powder 200 and sealed in the aperture 30a between the sealant layers 36, 37. As shown in FIG. 10, the upper member 50u can include a tab 150t that engages a slot 150s in the lower member 50l of the airway disk 50 for alignment and/or attachment.

FIG. 12 illustrates a dose container 30c on the outer row 31 being opened with the piercing member 100b and the associated curvilinear airflow path 41t, 51t. FIG. 14 illustrates the piercing member 100a in position to open a dose container 30c on the inner row 32 with the associated airflow path 41t, 51t.

Figure 15A:
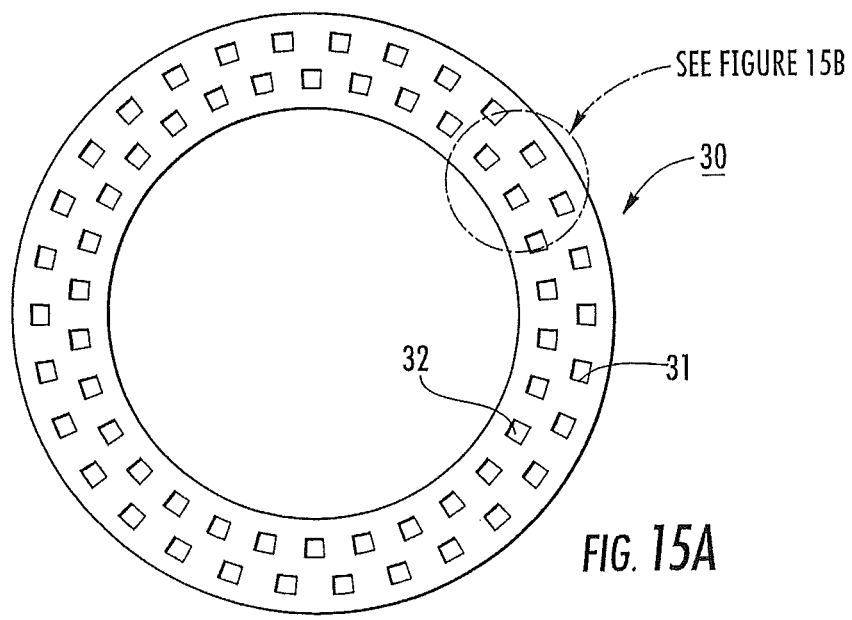
FIG. 15A is a top view of a dose container ring according to some embodiments of the present invention.
Figure 15B:
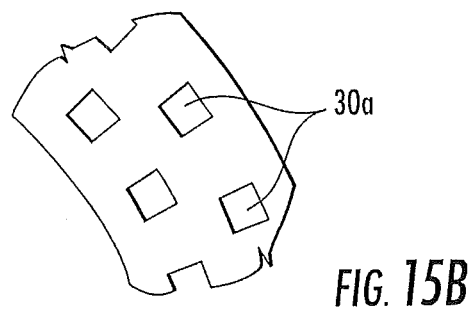
FIG. 15B is a partial enlarged fragmentary view of the ring shown in FIG. 15A.
Figure 16:
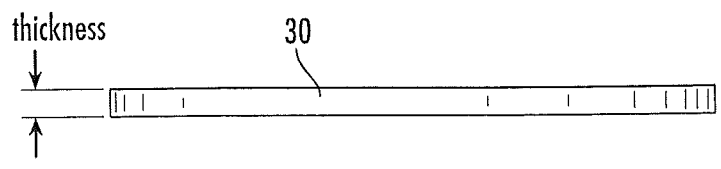
FIG. 16 is a side view of the ring shown in FIG. 15A.

FIGS. 15A, 15B and 16 illustrate an example of a dose container disk or ring 30 with two rows of apertures 30a used for dose containers 30c. The dose container disk 30 can be relatively thin, such as about 2-4 mm thick. The dose container apertures 30a can be configured so that the inner row 32 is at least about 2 mm from the outer row 31 and so that the inner and outer rows of dose containers are spaced inward from the respective perimeters by about 2 mm. This spacing can provide sufficient moisture permeability resistance and/or oxygen resistance.

FIG. 17A illustrates on embodiment of an inhaler 10 with a long exit air path 10l compared to the shorter flow path in FIG. 18A. In this embodiment, the airway disks can orient the channels 41, 51 so that the open ends 41b, 51b face and open to the inside of the disk rather than the outside. FIG. 17A also illustrates that the dose container disk 30 can be configured with blisters 130.

FIG. 17A also illustrates that the piercing mechanism 100 can comprise a rotating piercer head 102 configured to pierce a dose container 30c on the inner row, then rotate to pierce the adjacent one 30c on the outer row.

FIG. 18A illustrates that the inhaler 10 can be configured with a piercing mechanism 100 that moves radially to open a dose container 30c in one row then move radially inward or radially outward to open a dose container 30c in the other row. The dose container assembly 20 and/or one or more of the airway disks 40, 50 and dose container disk 30 can also be configured to axially or otherwise bias (together or individually) with a wall or walls of an exit airflow path to provide a sufficiently tight seal, such as discussed above. FIGS. 18A, 18B also illustrate that the inhaler 10 can include an indexing mechanism 109 that cooperates with the gear teeth 59 on the inner perimeter of the upper disk 50. Other indexing mechanisms may be used to rotate the assembly 20 to place the different dose containers 30c in the dispensing position.

FIG. 18C illustrates that the inhaler 10 can be configured with a piercing mechanism 100 that has two piercers 100a, 100b, one that pierces dose containers on the inner row and the other that pierces/opens dose containers on the outer row. Typically, the piercing mechanism 100 is configured so that a dose container, on the outer or inner row is pierced, then a dose container on the opposite row is pierced. The piercers 100a, 100b can reciprocate up and down to open the respective dose container. The dose container assembly 20 and/or one or more of the airway disks 40, 50 and dose container disk 30 can also be configured to axially or otherwise bias (together or individually) with a wall or walls of an exit airflow path to provide a sufficiently tight seal.

FIGS. 18C-18E also illustrate that the inhaler 10 can include an indexing mechanism 109 with gears 109g that cooperate with an indexing post 109p and the disk assembly 20 gear teeth 59a can reside on the inner perimeter of the lower disk 40. FIG. 18D is shown inverted from the normal use orientation shown in FIG. 18C. FIG. 18C-18E also show that the lower airway disk 40 can include two proximately stacked layers of gear teeth 59a, 59b, one of which 59a cooperates with the post 109p and associated indexing gears 109g and the other of which 59b can provide more precise positioning using arms 109r as shown in FIG. 18D. Other indexing mechanisms may be used to rotate the assembly 20 to place the different dose containers 30c in the dispensing position. The dual piercers 100a, 100b can cooperate with ramp surfaces (fins 211) on ramp disk 209. The fins 211 can be arranged as circumferentially offset fins on two concentric rows that force the respective piercers 100a, 100b down to pierce sealant 36 and/or 37 (FIG. 2E) in response to contact with the fins. Additional description of the indexer and dual piercer are provided in, co-assigned U.S. patent application Ser. No. 12/566,724, the contents of which are hereby incorporated by reference as if recited in full herein.

In some embodiments, the mouthpiece port 10p and an air inlet port (not shown) may be spaced apart about a distance of between about 12-127 mm (about 0.5-5 inches). The inhaler 10 may have a relatively short air intake airpath (measured from where an air intake is disposed to the inhalation port 10p), such as between about 12-25.4 mm such as shown in FIGS. 7A-7C, 18A and 18C, or a longer air path such as shown in FIG. 17A, typically between about 50-127 mm (about 2-5 inches). The shorter air path can be defined to include a short tubular air path extending between the dry powder release location and the inhalation mouthpiece with a turbulence promoter segment that inhibits agglomeration that merges into the inhaler mouthpiece (not shown). The longer air path may extend across a major portion or substantially all of a width or length of the inhaler body. The inner surfaces/shape of the flow path can be polygonal to facilitate a cyclonic air stream to bounce off the inner surfaces which act as impact surfaces. For additional discussion of suitable turbulence promoter configurations, see PCT/US2005/032492, entitled, Dry Powder Inhalers That Inhibit Agglomeration, Related Devices and Methods, the contents of which are hereby incorporated by reference as if recited in full herein.

The inhaler 10 can have a body that is a portable, relatively compact "pocket-sized" configuration. In some embodiments, the inhaler body can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body can also be configured to be generally planar on opposing primary surfaces to facilitate pocket storage.

The inhaler can include a circuit that can control certain operations of the inhaler 10. The inhaler 10 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 10 can be configured to via a wired or wireless communication link (one-way or two-way) to be able to communicate with a clinician or pharmacy for reorders of medicines and/or patient compliance. The inhaler 10 may also include a second peripheral device communication port (not shown). The inhaler 10 may be able to communicate via the Internet, telephone, cell phone or other electronic communication protocol.

In some embodiments, the circuit can include computer program code and/or computer applications that communicate additional data to a user (optionally to the display) as noted above and/or communicate with another remote device (the term "remote" including communicating with devices that are local but typically not connected during normal inhalant use).

In some embodiments, the circuit can be in communication with a vibrator device (not shown). The vibrator device can be any suitable vibrator mechanism. The vibrator device can be configured to vibrate the dry powder in the airflow path. In some embodiments, the vibrator device can comprise a transducer that is configured to vibrate the opened cartridge(s) holding the dry powder. Examples of vibrator devices include, but are not limited to, one or more of: (a) ultrasound or other acoustic or sound-based sources (above, below or at audible wavelengths) that can be used to instantaneously apply non-linear pressure signals onto the dry powder; (b) electrical or mechanical vibration of the walls (sidewalls, ceiling and/or floor) of the inhalation flow channel, which can include magnetically induced vibrations and/or deflections (which can use electromagnets or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electro-mechanical vibratory devices are described in U.S. Pat. Nos. 5,727,607, 5,909,829 and 5,947,169, the contents of which are incorporated by reference as if recited in full herein. Combinations of different vibrating mechanisms can also be used.

In some embodiments, the vibrator device can include a commercially available miniature transducer from Star Micronics (Shizuoka, Japan), having part number QMB-105PX. The transducer can have resonant frequencies in the range of between about 400-600 Hz.

In certain embodiments, the inhaler 10 can include visible indicia (flashing light or display "error" or alert) and/or can be configured to provide audible alerts to warn a user that a dose was properly (and/or improperly) inhaled or released from the inhaler. For example, certain dry powder dose sizes are formulated so that it can be difficult for a user to know whether they have inhaled the medicament (typically the dose is aerosolized and enters the body with little or no taste and/or tactile feel for confirmation). Thus, a sensor (not shown) can be positioned in communication with the flow path in an inhaler and configured to be in communication with a digital signal processor or microcontroller, each held in or on the inhaler. In operation, the sensor can be configured to detect a selected parameter, such as a difference in weight, a density in the exiting aerosol formulation, and the like, to confirm that the dose was released.

The sealed dose containers 30c can be configured so that the water vapor transmission rate can be less than about 1.0 g/100 in$^2$/24 hours, typically less than about 0.6 g/100 in$^2$/24 hours and an oxygen transmission rate that is suitable for the dry powder held therein. The dose container assemblies 20, 20' can be configured with a stable shelf life of between about 1-5 years, typically about 4 years.

The dose containers 30c can have a volume (prior to filling and sealing) that is less than about 24 mm$^3$, typically between 5-15 mm$^3$. The powder bulk density can be about 1 g/cm$^3$ while the power nominal density when filled (for reference) can be about 0.5 g/cm$^3$. The maximum compression of a drug by filling and sealing in the dose container 30c can be less than about 5%, typically less than about 2%. The maximum heating of drug during the filling and sealing can be maintained to a desirable level so as not to affect the efficacy of the drug or the formulation.

Figure 21:
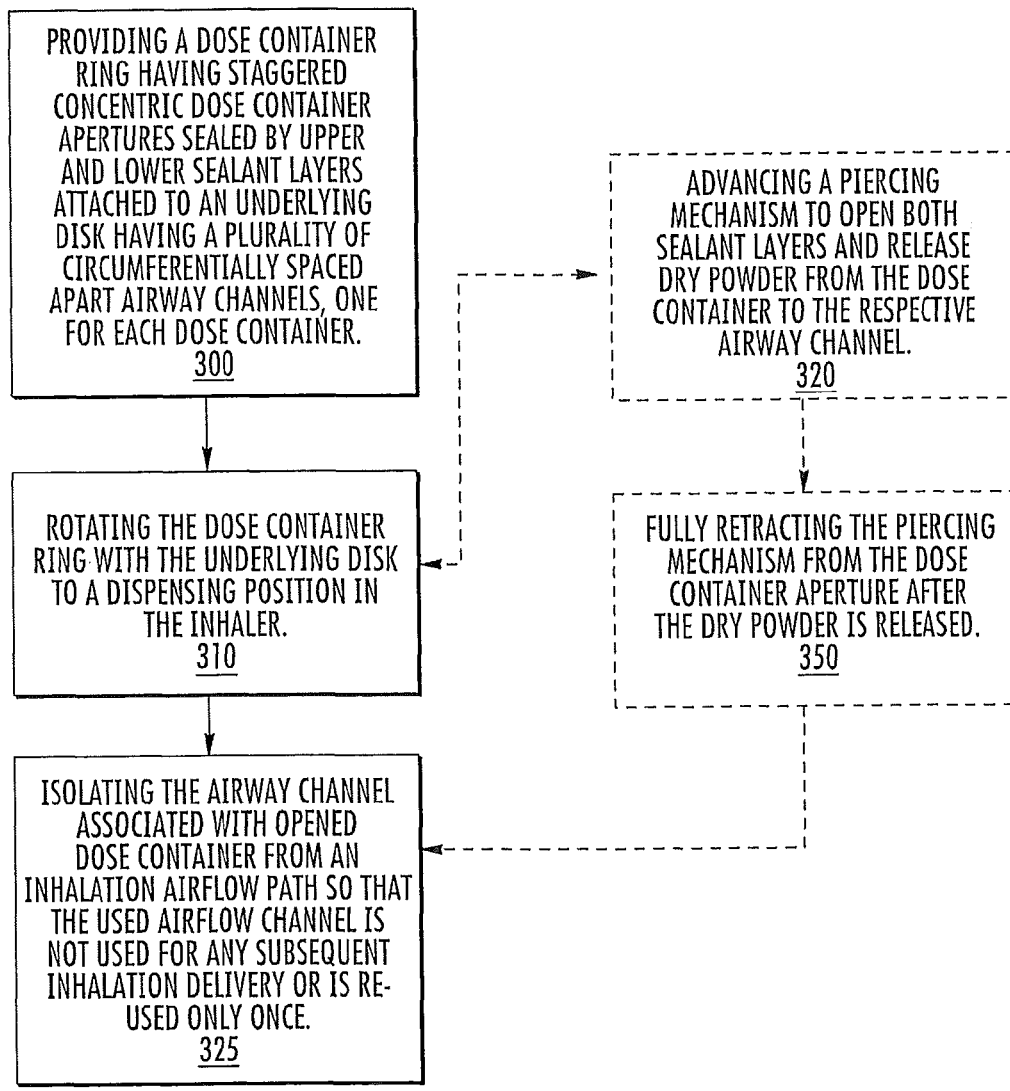
FIG. 21 is a flow chart of exemplary operations that can be used to operate an inhaler according to some embodiments of the present invention.

FIG. 21 illustrates exemplary operations that can be used to operate an inhaler according to embodiments of the present invention. The device can be configured to have an automated three-stage operation at actuation to inhibit overdose delivery, e.g., it can serially: (a) pierce the sealant layers, (b) release the drug (typically followed close in time by delivery to a user), and (c) index to the next (unopened) dose container (thus isolating or closing any exit route for the released dry powder if not inhaled); or (a) index to a target dose container (thus isolating an earlier opened airway channel), (b) pierce the sealant layers and (c) release drug or dry powder from the opened dose container. A dose container ring having a staggered concentric arrangement of dose container apertures sealed by upper and lower sealant layers defining dose containers and attached to an underlying disk with a plurality of circumferentially spaced apart airway channels, one for each dose container, is provided (block 300). The dose container with the underlying disk is rotated to a dispensing position in the inhaler (block 310). The indexing can rotate the dose disk assembly about 6 degrees, repeated about 60 times to access 30 dose containers on the inner row and 30 dose containers on the outer row while rotating only about 360 degrees. The airway channel associated with the released dry powder is isolated from the inhalation path so that the used airflow channel is not used for any subsequent inhalation delivery or is used only one more time (block 325).

In some embodiments, a piercing mechanism is advanced to open both sealant layers and release dry powder from the dose container in the dispensing position to the underlying airway channel (block 320). The piercing mechanism can either remain extended or can be partially or fully retracted with the piercing mechanism or cooperating member thereof occluding the opening to the upper airway channel. In some embodiments, the piercing mechanism can be partially retracted, leaving at least a forward portion in the respective dose container aperture to occlude and/or plug the aperture. The isolating step can be in response to and/or after either the step of fully retracting the piercing mechanism from the dose container aperture (block 350) or the rotating step (block 310) or both.

The method can also optionally include flowably directing the released dry powder to a user via the airway channel.

Figure 22:
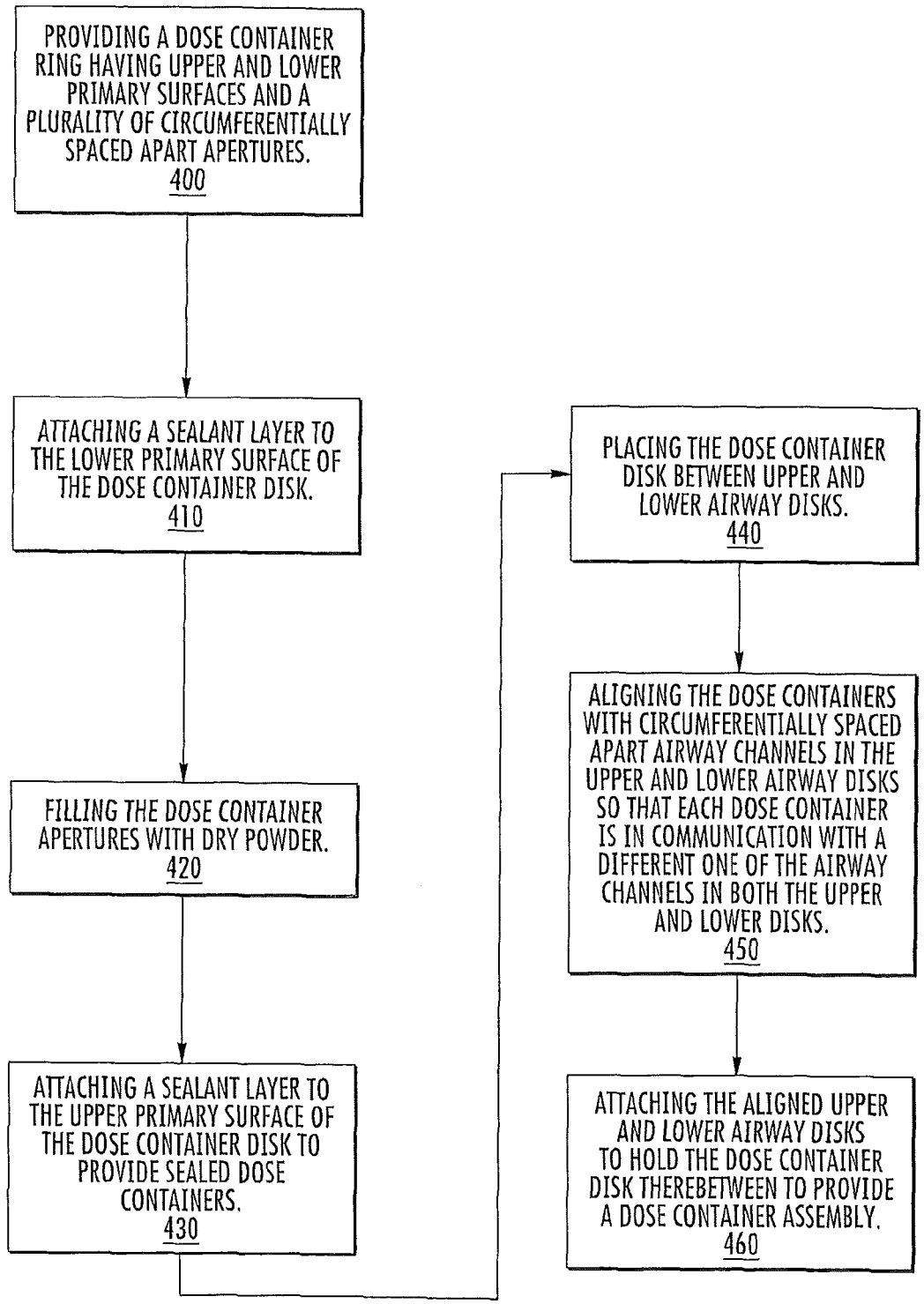
FIG. 22 is a flow chart of operations that can be used to fabricate or assemble a dose container assembly according to some embodiments of the present invention.

FIG. 22 illustrates exemplary fabrication operations that can be used to assemble a dose container assembly according to embodiments of the present invention. As shown, a dose container disk (block 400) with circumferentially spaced apart through apertures is provided. At least one sealant layer is attached to the upper or lower primary surface of the disk over or under the dose container apertures (block 410) (e.g., a continuous layer or strips or small pieces of sealant layers can be positioned over the apertures). The dose container apertures are filled with dry powder (noting "filled" does not require volumetrically full) (block 420). Typically, the powder is filled to between about 30-75% volume. The sealant layer can be attached to the other primary surface of the dose disk to provide sealed dose containers (block 430). The dose container disk can be placed between upper and lower airway disks (block 440). The dose containers can be aligned with circumferentially spaced apart airway channels on the airway disks so that each dose container is in communication with a different one of the airway channels in both the upper and lower disks (block 450). The upper and lower disks can be attached to hold the dose container disk therebetween to provide a dose container assembly (block 460).

The following exemplary claims are presented in the specification to support one or more devices, features, and methods of embodiments of the present invention. While not particularly listed below, Applicant preserves the right to claim other features shown or described in the application.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such That which is claimed is:

1. A method of operating an inhaler, comprising:
providing a dose container ring having staggered concentric dose containers with dose container apertures sealed by upper and lower sealant layers over and under the dose container apertures to define sealed dose containers attached to at least one airway disk, the at least one airway disk comprising one or both of an underlying or overlying airway disk having a plurality of circumferentially spaced apart airway channels, wherein at least one dose container of the staggered concentric dose containers is aligned with each of the plurality of circumferentially spaced apart airway channels;
rotating the dose container ring and the at least one airway disk together to present a first dose container of the staggered concentric dose containers and a corresponding first airway channel of the circumferentially spaced apart airway channels of the airway disk to a dispensing position in the inhaler;
advancing a piercing mechanism to open the upper and lower sealant layers of the first dose container and release dry powder from the first dose container to the corresponding first airway channel;
delivering the released dry powder from the first dose container to a user via inhalation through the first airway channel into an inhalation exit flow path in the inhaler; and
isolating the first airway channel from the inhalation flow path so that the first airway channel is reused only once for a different dose container of the staggered concentric dose containers or is not used for any subsequent inhalation delivery of a different dose container of the staggered concentric dose containers.

2. A method according to claim 1, further comprising, after the advancing of the piercing mechanism to open the upper and lower sealant layers of the first dose container, partially or fully retracting the piercing mechanism while leaving at least a forward portion of the piercing mechanism in an airway associated with the inhalation exit flow path and/or in an airway disk aperture associated with the at least one airway disk during the delivering of the released dry powder from the first dose container to the user via inhalation through the inhalation exit flow path in the inhaler.

3. A method according to claim 1, further comprising fully retracting the piercing mechanism from an airway aperture associated with the inhalation exit flow path and/or an airway disk aperture of the at least one airway disk after the delivering of the released dry powder from the first dose container to the user via inhalation through the inhalation exit flow path in the inhaler.

4. A method according to claim 1, wherein the isolating of the first airway channel is carried out in response to fully retracting the piercing mechanism by automatically indexing the dose container ring when the piercing mechanism is fully retracted.

5. A method according to claim 1, further comprising, after the advancing of the piercing mechanism to open the upper and lower sealant layers of the first dose container, flowably directing the released dry powder from the first dose container to the user via inhalation out of a mouthpiece from the first airway channel before fully retracting the piercing mechanism from the first dose container and/or an aligned airway aperture in the at least one airway disk.

6. A method according to claim 1, wherein the staggered concentric dose containers are arranged in front and back rows, and wherein the advancing of the piercing mechanism is carried out to serially open either (a) the first dose container on the front row, then a second dose container on the back row or (b) the first dose container on the back row then a second dose container on the front row.

7. A method of fabricating a dose container assembly, comprising:
providing a dose container disk having upper and lower primary surfaces with a plurality of circumferentially spaced apart apertures;
attaching a sealant layer to one of the upper or lower primary surfaces of the dose container disk;
filling the circumferentially spaced apart apertures of the dose container disk with dry powder;
attaching a sealant layer to a different one of the upper or lower primary surface of the dose container to provide sealed dose containers;
providing at least one airway disk;
aligning the circumferentially spaced apart dose containers with circumferentially spaced apart, radially extending, elongate airway channels extending across the at least one airway disk so that each of the circumferentially spaced apart dose containers is in communication with at least one of the circumferentially spaced apart, elongate radially extending airway channels in the at least one airway disk; and
assembling the aligned at least one airway disk to the dose container disk to provide a dose container assembly.

8. A method according to claim 7, wherein the step of providing at least one airway disk is carried out by providing two airway disks, an upper airway disk and a lower airway disk, and wherein the aligning the circumferentially spaced apart dose containers with the circumferentially spaced apart airway channels on the at least one airway disk is carried out so that the circumferentially spaced apart dose containers are aligned with the circumferentially spaced apart airway channels of both the upper and lower airway disks so that each dose container is in communication with a single one of the circumferentially spaced apart airway channels in both the upper and lower disks.

9. A method according to claim 8, wherein the step of assembling is carried out by press-fitting the upper and lower airway disks together and sandwiching the dose container disk snugly therebetween so that the circumferentially spaced apart airway channels of the upper and lower airway disks define substantially airtight interfaces with the circumferentially spaced apart apertures of the dose container disk.

10. A method according to claim 7, wherein the elongate channels have opposing first and second end portions, with the first end portion being substantially open and the second end portion being totally or substantially closed, and wherein the first end portion resides at an inner or outer perimeter of the at least one airway disk and the second end portion resides above or below a respective dose container.

11. A method of operating an inhaler, comprising:
providing a dose container ring having staggered concentric dose containers with dose container apertures sealed by upper and lower sealant layers over and under the dose container apertures to define sealed dose containers attached between upper and lower airway disks, the upper and lower airway disks comprising a plurality of circumferentially spaced apart, elongate and radially extending airway channels;
rotating the dose container ring and the at least one airway disk together to present a first dose container of the staggered concentric dose containers and a corresponding pair of first airway channels of the circumferentially spaced apart airway channels of the upper and lower airway disks to a dispensing position in the inhaler;
advancing a piercing mechanism to open the upper and lower sealant layers of the first dose container and release dry powder from the first dose container to the corresponding first airway channel in the lower airway disk;
delivering the released dry powder from the first dose container to a user via inhalation to an inhalation exit flow path comprising the first airway channel in the lower and/or upper airway disk in the inhaler; and
isolating the pair of first airway channels of the upper and lower airway disks from the inhalation flow path so that the first airway channels of the upper and lower airway disk are reused only once for a different dose container of the staggered concentric dose containers or are not used for any subsequent inhalation delivery of a different dose container of the staggered concentric dose containers.

12. The method of claim 11, further comprising, after the advancing of the piercing mechanism to open the upper and lower sealant layers of the first dose container, partially or fully retracting the piercing mechanism while leaving at least a forward portion of the piercing mechanism in an airway associated with the inhalation exit flow path and/or in an airway disk aperture associated with the upper airway disk during the delivering of the released dry powder from the first dose container to the user via inhalation through the inhalation exit flow path in the inhaler.

13. The method of claim 11, wherein the upper airway disk comprises a plurality of circumferentially spaced apart staggered concentric downwardly extending open apertures with the staggered concentric dose containers, and wherein the advancing the piercing mechanism is carried out by extending a piercer through a first aperture of the open apertures of the staggered concentric airway disk apertures then through the upper and lower sealant layers of the first dose container and partially retracting the piercer so that the piercer remains in the first airway disk aperture during the delivering of the released dry powder.

14. The method of claim 11, wherein the elongate channels have opposing first and second end portions, with the first end portion being substantially open and the second end portion being substantially or totally closed, and wherein the first end portion resides at an inner or outer perimeter of the upper and lower airway disk and the second end portion resides above or below a respective dose container.

* * * * *